United States Patent [19]

Green et al.

[11] Patent Number: 5,554,169
[45] Date of Patent: Sep. 10, 1996

[54] METHOD FOR PLACING STAPLES IN LAPAROSCOPIC OR ENDOSCOPIC PROCEDURES

[75] Inventors: David T. Green, Westport; Henry Bolanos, East Norwalk; Daniel E. Alesi, New Fairfield; Keith Ratcliff, Sandy Hook; Charles R. Sherts, Southport, all of Conn.

[73] Assignee: United States Surgical Corporation, Norwalk, Conn.

[21] Appl. No.: 469,938

[22] Filed: Jun. 6, 1995

Related U.S. Application Data

[63] Continuation of Ser. No. 145,727, Oct. 29, 1993, Pat. No. 5,425,745, which is a continuation of Ser. No. 943,383, Sep. 10, 1992, abandoned, which is a continuation of Ser. No. 709,641, Jun. 3, 1991, abandoned, which is a division of Ser. No. 358,646, May 26, 1989, Pat. No. 5,040,715.

[51] Int. Cl.⁶ ............................................. A61B 17/04
[52] U.S. Cl. .................... 606/219; 606/143; 227/19
[58] Field of Search ............................... 606/219, 142, 606/143; 227/19, 175–180

[56] References Cited

U.S. PATENT DOCUMENTS

| | | |
|---|---|---|
| Re. 28,932 | 8/1976 | Noiles et al. ........................ 227/19 |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,499,591 | 3/1970 | Green . |
| 3,593,903 | 7/1971 | Astafiev et al. ...................... 227/19 |
| 3,675,688 | 7/1972 | Bryan et al. . |
| 3,735,762 | 5/1973 | Bryan et al. . |
| 3,777,538 | 12/1973 | Weatherly et al. ................. 606/142 |
| 3,819,100 | 6/1974 | Noiles et al. . |
| 3,844,289 | 10/1974 | Noiles ................................. 227/19 |
| 3,949,924 | 4/1976 | Green .................................. 227/19 |
| 4,027,510 | 6/1977 | Hiltebrandt . |
| 4,060,089 | 11/1977 | Noiles . |
| 4,064,881 | 12/1977 | Meredith . |
| 4,086,926 | 5/1978 | Green et al. . |
| 4,111,206 | 9/1978 | Vishnevsky et al. . |
| 4,169,476 | 10/1979 | Hiltebrandt . |
| 4,202,480 | 5/1980 | Annett . |
| 4,256,251 | 3/1981 | Moshofsky . |
| 4,273,129 | 6/1981 | Boebel . |
| 4,325,377 | 4/1982 | Boebel . |
| 4,383,634 | 5/1983 | Green . |
| 4,391,401 | 7/1983 | Moshofsky ................................. 227/19 |
| 4,402,445 | 9/1983 | Green ........................................ 227/19 |

(List continued on next page.)

FOREIGN PATENT DOCUMENTS

| | | |
|---|---|---|
| 0369324 | 5/1990 | European Pat. Off. . |
| 51-149985 | 5/1976 | Japan . |
| 728848 | 5/1980 | U.S.S.R. . |
| 1352554 | 5/1974 | United Kingdom . |
| 1452185 | 10/1976 | United Kingdom . |
| 2048685 | 12/1980 | United Kingdom . |
| 2165559 | 4/1986 | United Kingdom . |

OTHER PUBLICATIONS

Article, Swain, C. P. and Mills, T. N. "An Endoscopic Sewing Machine," Gastrointestinal Endoscope, 1986, vol. 32, No. 1, pp. 36–38.

Article, Swain, S. P., Brown, G. J. and Mills, T. N. "An Endoscopic Stapling Device: The Development of a New Flexible Endoscopically Controlled Device for Placing Multiple Transmural Stapless in Gastrointestinal Tissue," Gastrointestinal Endoscopy, 1989, vol. 35, No. 4, pp. 338–339.

*Primary Examiner*—Gary Jackson

[57] ABSTRACT

A surgical stapler for placing lateral lines of staples and making an incision, all through an endoscopic tube, includes an anvil member which is mounted to the distal end of an elongated housing. A tubular collar disposed around the arm of the anvil member is movable to a distal position to bias the anvil member and a cartridge assembly into cooperative alignment, thereby clamping body tissue to be fastened between the anvil member and cartridge assembly.

2 Claims, 26 Drawing Sheets

U.S. PATENT DOCUMENTS

| | | |
|---|---|---|
| 4,429,695 | 2/1984 | Green . |
| 4,473,077 | 9/1984 | Noiles et al. . |
| 4,506,670 | 3/1985 | Crossley . |
| 4,506,671 | 3/1985 | Green . |
| 4,513,746 | 4/1985 | Aranyi et al. . |
| 4,519,532 | 5/1985 | Foslien . |
| 4,520,817 | 6/1985 | Green . |
| 4,534,352 | 8/1985 | Korthoff ................................. 227/19 |
| 4,566,620 | 1/1986 | Green et al. . |
| 4,573,468 | 3/1986 | Conta et al. ............................. 227/19 |
| 4,573,622 | 3/1986 | Green et al. . |
| 4,576,167 | 3/1986 | Noiles . |
| 4,580,712 | 4/1986 | Green . |
| 4,589,416 | 5/1986 | Green . |
| 4,591,085 | 5/1986 | Di Giovanni . |
| 4,606,343 | 8/1986 | Conta et al. . |
| 4,610,383 | 9/1986 | Rothfuss et al. . |
| 4,633,861 | 1/1987 | Chow et al. . |
| 4,633,874 | 1/1987 | Chow ..................................... 227/19 |
| 4,646,745 | 3/1987 | Noiles . |
| 4,664,305 | 5/1987 | Blake, III et al. . |
| 4,714,187 | 12/1987 | Green . |
| 4,715,520 | 12/1987 | Roehr, Jr. et al. . |
| 4,728,020 | 3/1988 | Green et al. . |
| 4,744,365 | 5/1988 | Kaplan et al. . |
| 4,784,137 | 11/1988 | Kulik et al. . |
| 4,809,898 | 3/1989 | Gassner et al. . |
| 4,819,853 | 4/1989 | Green . |
| 4,821,942 | 4/1989 | Richards et al. . |
| 4,839,130 | 6/1989 | Kaplan et al. ............................ 227/19 |
| 4,841,888 | 6/1989 | Mills et al. . |
| 4,844,854 | 7/1989 | Kaplan et al. . |
| 4,848,637 | 7/1989 | Pruitt . |
| 4,858,608 | 8/1989 | McQuilkin . |
| 4,873,977 | 10/1989 | Avant et al. . |
| 4,932,960 | 6/1990 | Green et al. . |
| 4,941,623 | 7/1990 | Pruitt . |
| 4,944,443 | 7/1990 | Oddsen et al. . |
| 4,955,959 | 9/1990 | Tompkins et al. . |
| 4,978,049 | 12/1990 | Green . |
| 5,031,814 | 7/1991 | Tompkins et al. ........................ 227/19 |
| 5,040,715 | 8/1991 | Green et al. . |
| 5,071,430 | 12/1991 | de Salis et al. . |

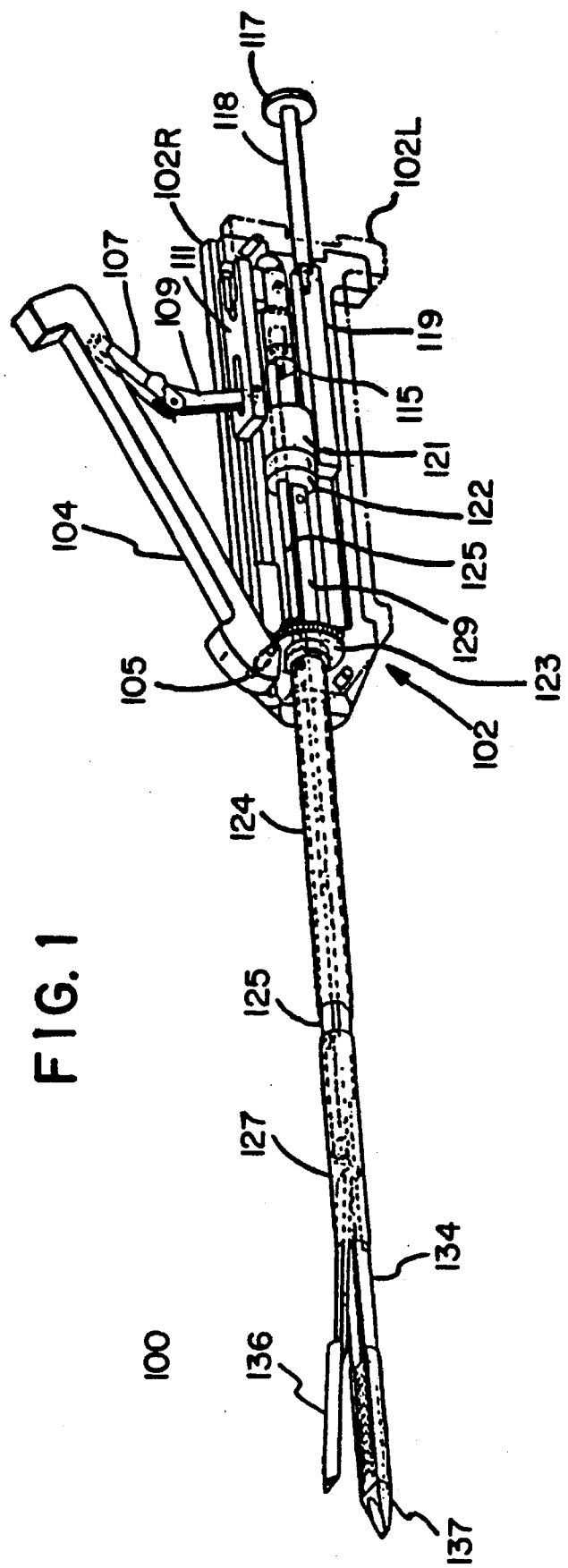

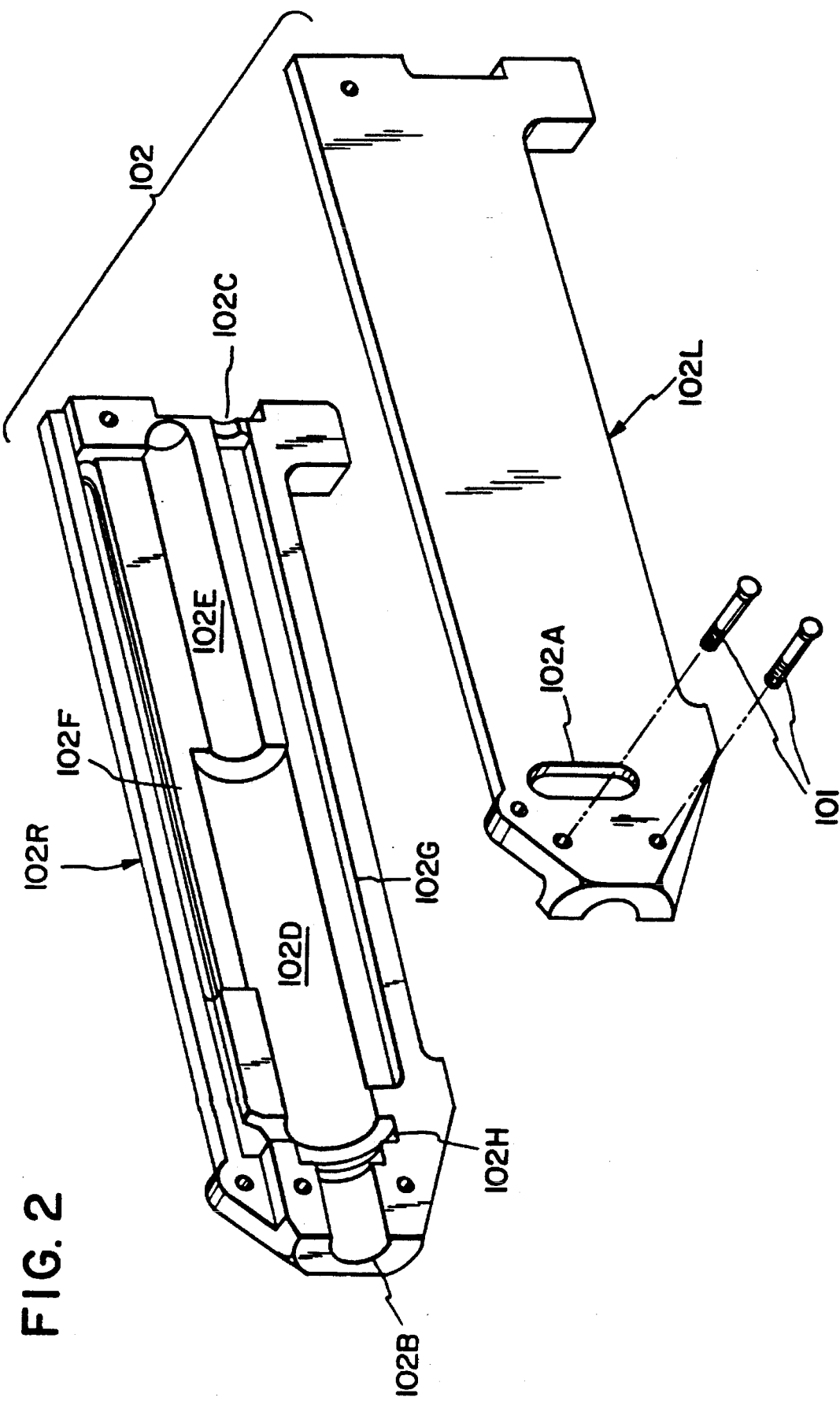

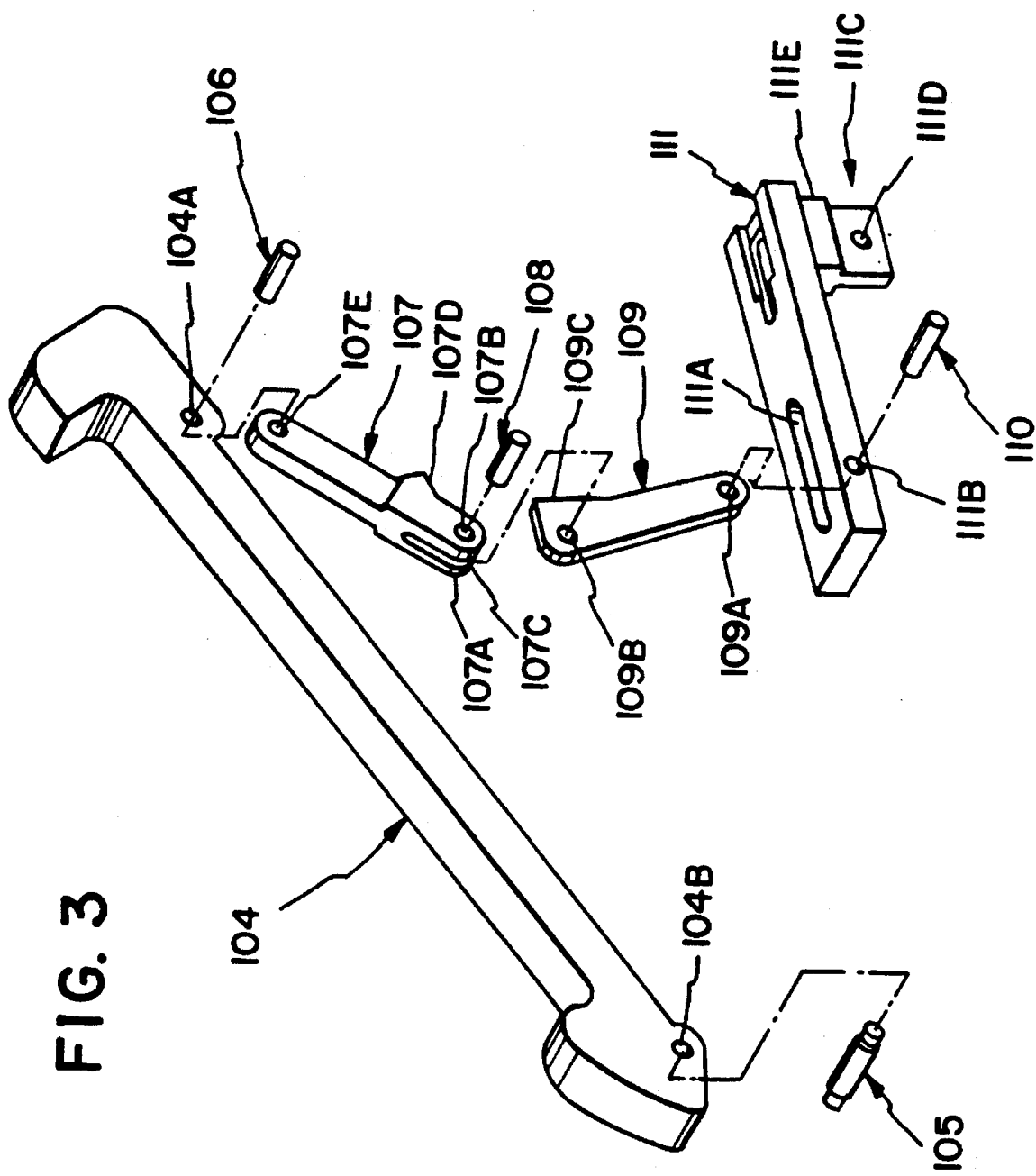

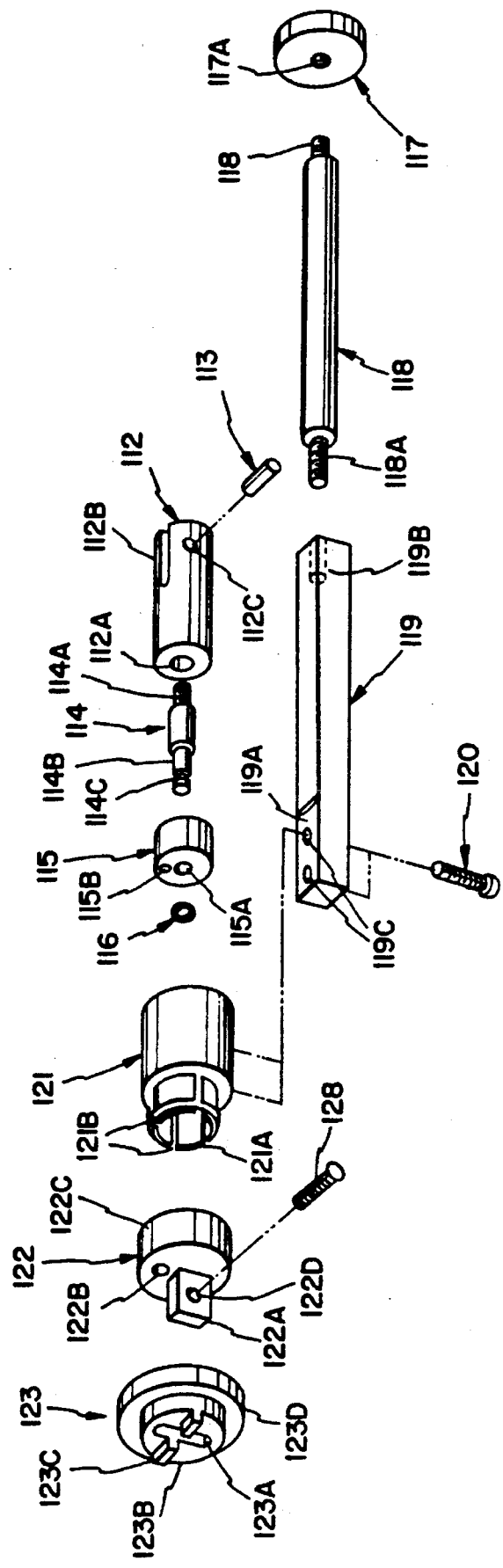

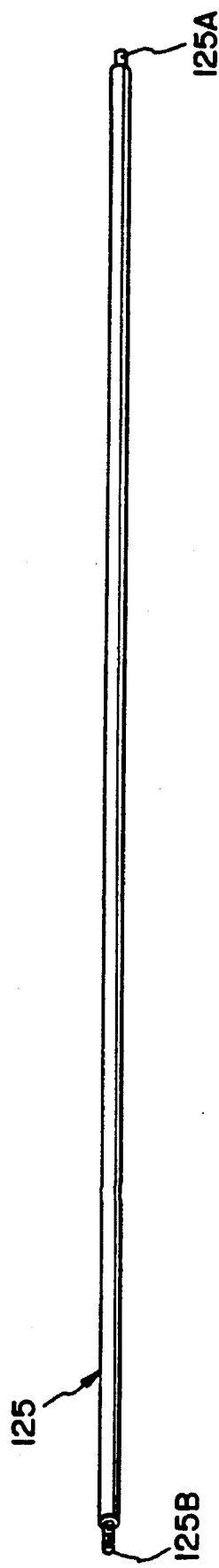
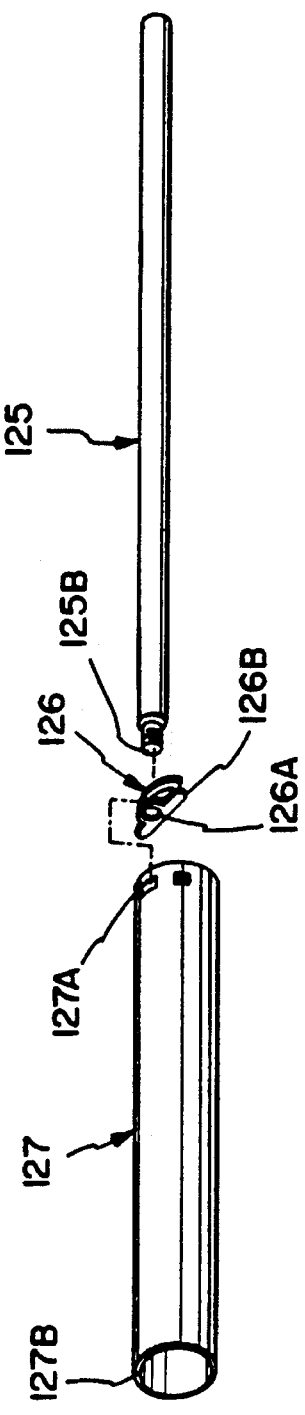
FIG. 6
FIG. 7

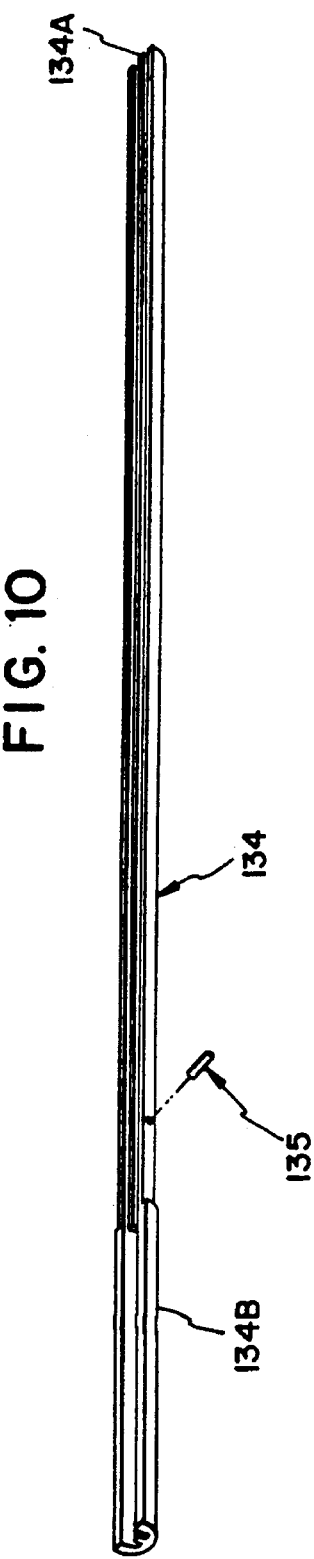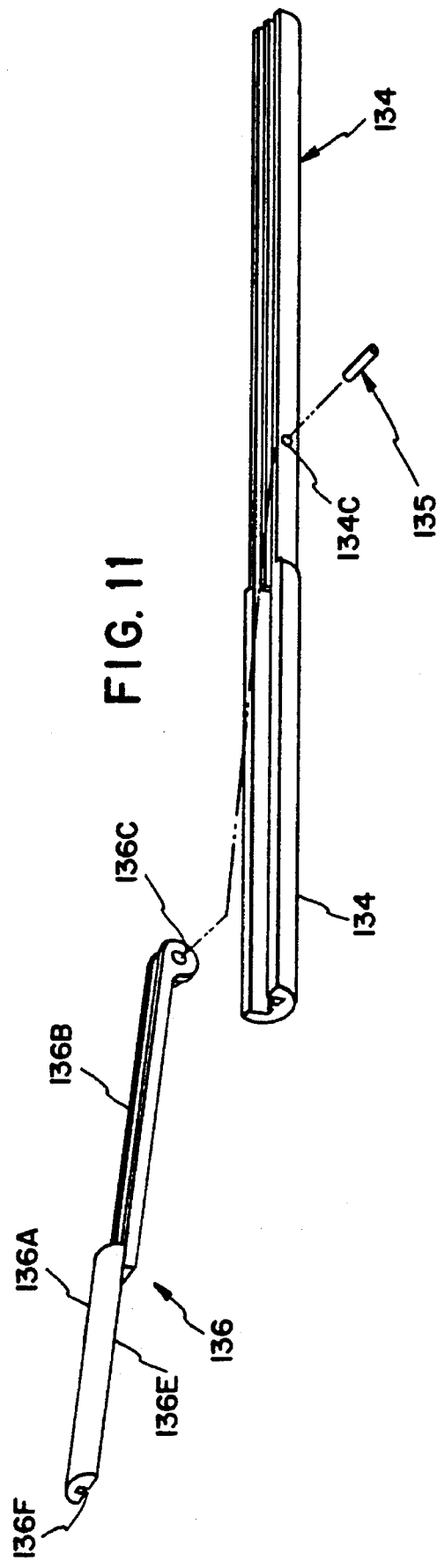

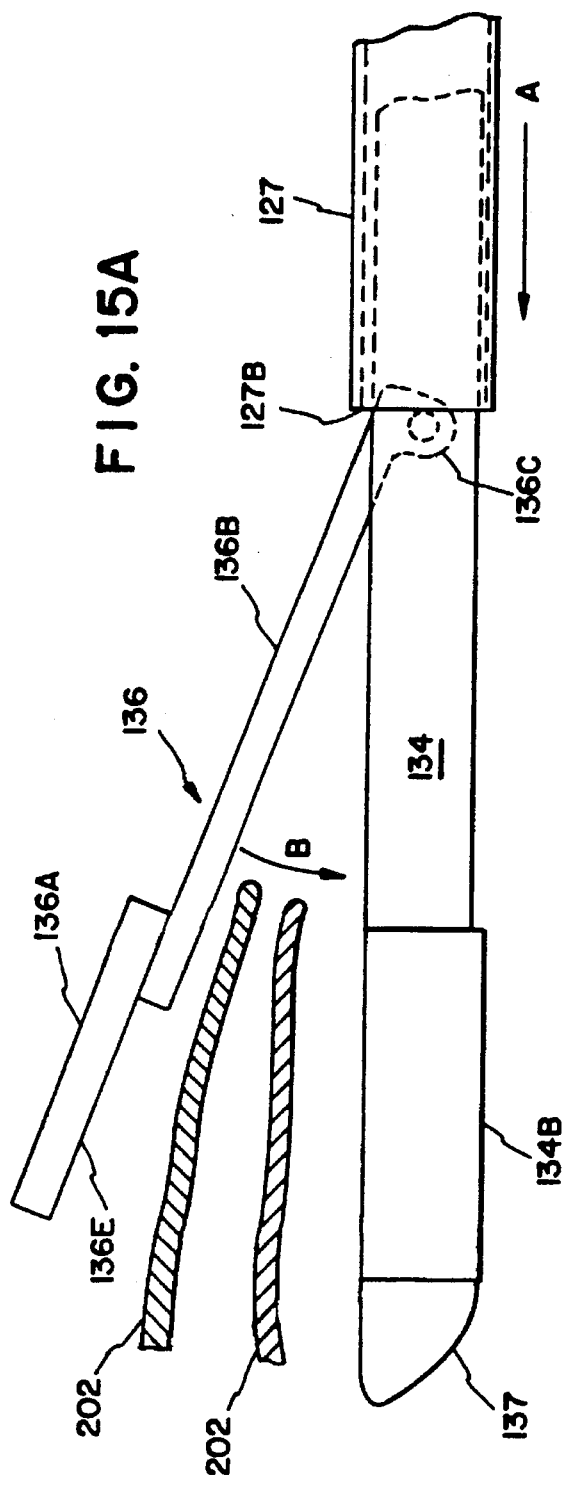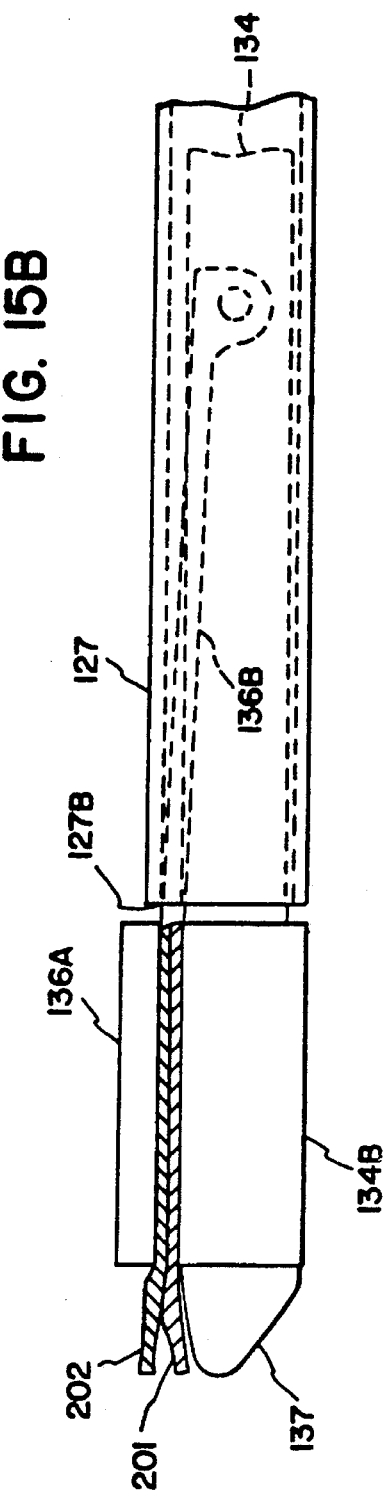

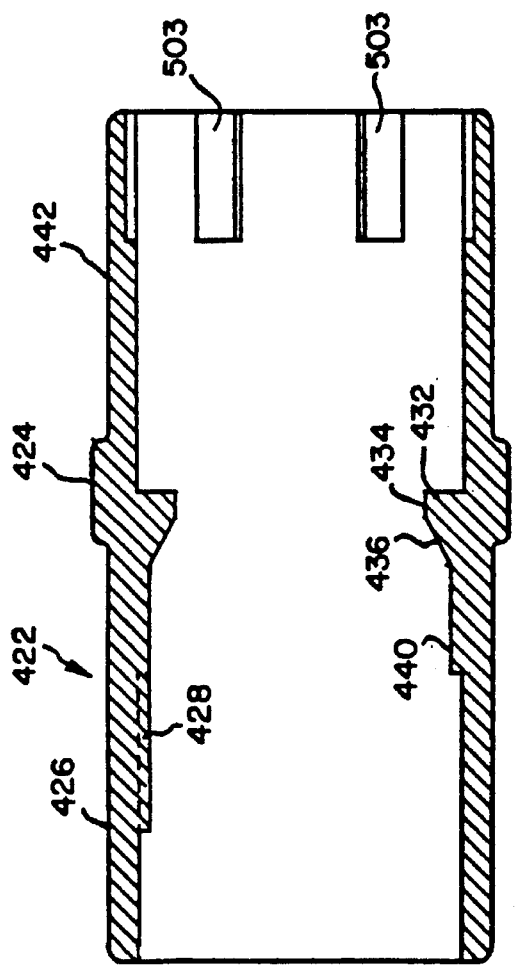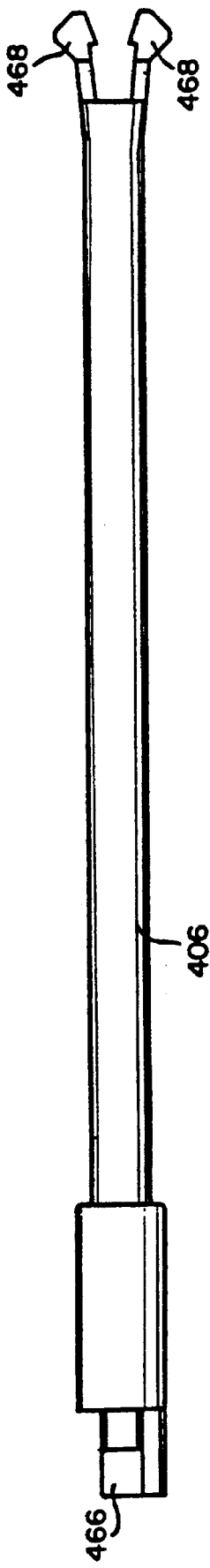

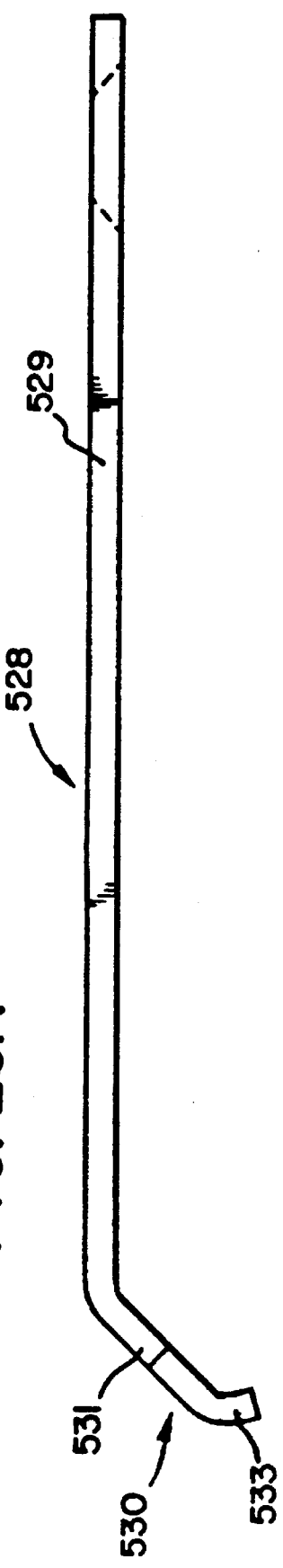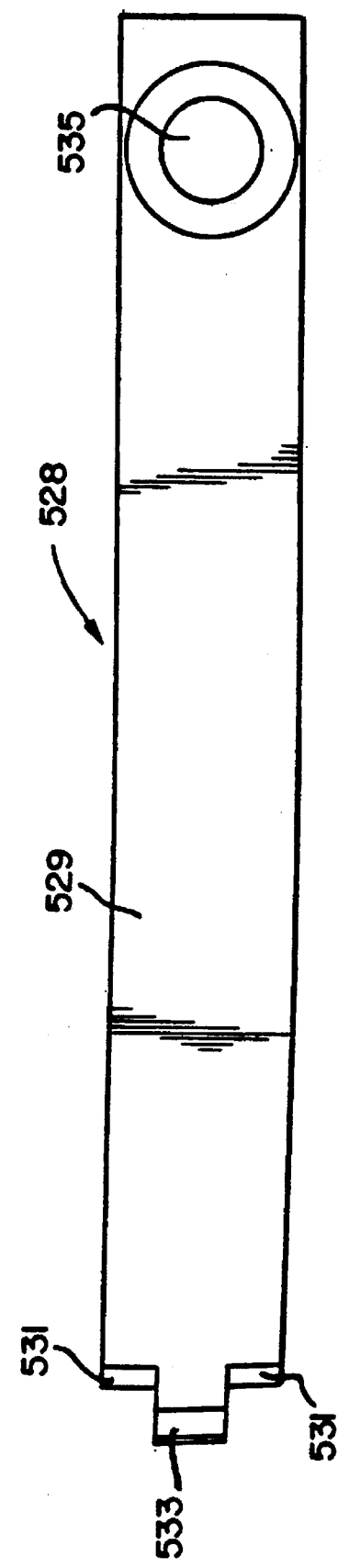
FIG. 28A
FIG. 28B

METHOD FOR PLACING STAPLES IN LAPAROSCOPIC OR ENDOSCOPIC PROCEDURES

This is a continuation of U.S. application Ser. No. 08/145,727 filed Oct. 29, 1993, now U.S. Pat. No. 5,425,745 which is a continuation of U.S. Ser. application No. 07/943,383 filed Sep. 10, 1992, now abandoned, which is a continuation of Ser. No. 07/709,641 filed Jun. 3, 1991, now abandoned, which is a divisional of Ser. No. 07/358,646 filed May 26, 1989, now U.S. Pat. No. 5,040,715.

BACKGROUND OF THE INVENTION

1. Field of the Invention

This invention relates to surgical stapling apparatus, and more particularly to a surgical stapler for mechanically effecting a plurality of lines of stitching staples in body tissue.

2. Background of Related Art

In some surgical operations it is necessary to adjoin two hollow body organs alongside each other, generally with their longitudinal axes parallel to each other, and to effect a longitudinal cut through the contacting circumferential walls of the two organs so that the two organs constitute a single hollow chamber along the length of the cut. Correspondingly, the circumferential portions of the two adjoining organs on each lateral side of the cut must be sutured by at least one line of "stitches" in order to maintain the integrity of the union.

Instruments for this purpose can comprise two elongated fingers which are respectively insertable into each organ from an open end thereof, the two fingers thereby having between them the two adjoining walls of the organs. Typically, one of the fingers carries a disposable cartridge housing a plurality of staples arranged in at least two lateral rows while the other finger comprises an anvil for curling the staple legs into hook form upon their being driven against the anvil. The stapling operation is effected by a pusher which travels longitudinally along the cartridge carrying finger extending into one organ, with the pusher acting upon the staples to place rows of staples in body tissue. Immediately behind the pusher and laterally positioned between the staple rows is a knife which severs the facing adjoining walls of the two organs to thereby longitudinally open the two organs to each other between the rows of staples.

One such instrument is disclosed in Bobrov et al. (U.S. Pat. No. 3,079,606). The instrument disclosed therein comprises an apparatus for simultaneously making a longitudinal incision and applying a row of staples on both sides of the incision. A further improvement is disclosed in Green (U.S. Pat. No. 3,490,675).

A later development disclosed in Green (U.S. Pat. No. 3,499,591) applies a double row of staples on each side of the incision. This is accomplished by a cartridge assembly wherein a cam member moves within a guide path between two sets of staggered staple carrying grooves. Staple drive members located within the grooves each have two staple pusher plates, and sloping surfaces disposed within the guide path so as to be contacted by the longitudinally moving cam and be driven along the groove to effect ejection of two staples.

These above-mentioned instruments comprise upper and lower frames which must be assembled before use, and disassembled after use. Such instruments have been used successfully in surgical operations requiring the placement of gastrointestinal anastamosis, but they require the surgeon to have direct manual access to the operation site.

However, in laparoscopic procedures surgery is performed through a small incision, and in endoscopic procedures surgery is performed through narrow endoscopic tubes inserted through small entrance wounds in the skin. Up to now there have been no instruments for placing lateral staple lines in laparoscopic or endoscopic procedures. Nor has there been any instrument suitable for placing lateral lines of staples and cutting tissue therebetween in laparoscopic or endoscopic procedures.

Because endoscopic procedures are more common than laparoscopic procedures, the present invention shall be discussed in terms of endoscopic procedures and apparatus. However, use herein of terms such as "encloseopic", "endoscopically" and "endoscopic portion", among others, should not be construed to limit the present invention to a stapling and cutting apparatus for use only in conjunction with an encloseopic tube. To the contrary, it is believed the present invention may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein.

3. Objects of the Invention

Accordingly, it is one object of the present invention to provide a surgical stapling apparatus for a method of endoscopically driving fasteners into body tissue.

It is another object of the present invention to utilize a surgical stapling apparatus which can adjoin hollow body organs alongside each other.

It is yet a further object of the present invention to utilize a surgical stapling apparatus which can be used endoscopically.

Another object of the present invention is to provide a surgical stapling and cutting apparatus which can be used endoscopically.

These and further objects and advantages are achieved by utilizing a surgical stapling apparatus insertable through a small incision or narrow tube for driving surgical fasteners into body tissue and cutting the body tissue between rows of staples.

SUMMARY OF THE INVENTION

In accordance with the present invention a surgical stapling apparatus is provided for placing one or more rows of staples endoscopically. Advantageously, a stapler apparatus constructed in accordance with the invention may further include a knife for making an incision in body tissue between rows of staples. The latter configuration may find particular use in adjoining two hollow organs or in removing an organ, such as the appendix.

Briefly stated, the surgical stapler in accordance with the invention comprises:

a) a frame;

b) a tubular portion defining a longitudinal axis and extending distally from said frame, said tubular portion including:

i) an elongated housing having means for mounting a cartridge assembly, said cartridge assembly including a plurality of surgical fasteners mounted therein, and having a tissue engaging surface;

ii) an anvil member having a fastener forming surface, said anvil member mounted to said elongated housing;

iii) means for effecting relative movement between said cartridge assembly and said anvil member; and iv) means for ejecting said surgical fasteners from said cartridge assembly, whereby said fasteners engage said fastener forming surface.

In one embodiment of the invention the frame and endoscopic portion of the instrument are reusable with replaceable staple carrying cartridges.

In another embodiment of the invention the endoscopic portion is formed as a disposable unit detachable from a reusable handle portion including the frame.

In yet a further embodiment of the invention, the entire instrument may be constructed as a single-use, disposable unit.

According to the method of the present invention, the endoscopic portion of the apparatus is inserted into the body through a small incision or, more likely, through an endoscopic tube. With the anvil member in the open position, body tissue is disposed between the anvil member and the tissue engaging surface of the cartridge assembly. The anvil is then closed against the cartridge to clamp the body tissue between the anvil and cartridge. The instrument is fired so that staples ejected from the cartridge penetrate through the body tissue and are formed closed against the anvil. Where appropriate, a knife forms an incision between several rows of staples. After the instrument has been fired, the clamping action of the anvil and cartridge assembly is released and the endoscopic portion of the instrument is withdrawn from the body.

The present invention advantageously permits a surgeon to perform internal stapling and cutting procedures without full access to the stapling site. Surprisingly, the stapling and cutting instrument in accordance with the invention may be inserted through a small incision or tube in order to place multiple staple lines and make an incision in the stapled tissue between several rows of staples.

The ability to perform stapling and cutting procedures through a small incision or tube remarkably reduces blood loss, tissue trauma and patient recovery time, contributing to improved health care practices.

BRIEF DESCRIPTION OF THE DRAWINGS

FIG. 1 illustrates a perspective cutaway view of the invention;

FIG. 2 illustrates an exploded view of the frame;

FIG. 3 illustrates an exploded view of the toggle lever actuating means;

FIG. 4 illustrates an exploded view of the interior actuating means;

FIGS. 6 and 7 show the collar shaft and collar;

FIGS. 10 and 11 illustrate the housing and anvil;

FIGS. 15A and 15B illustrate the clamping action of the instrument;

FIG. 20 illustrates a sectional side view of the sleeve in accordance with the first alternative embodiment of the invention;

FIG. 23 illustrates a side view of the channel adaptor of the first alternative embodiment of the invention;

FIGS. 28A and 28B illustrate top and front views, respectively, of a frame leaf spring;

DETAILED DESCRIPTION OF THE PREFERRED EMBODIMENTS

Figure 4A:
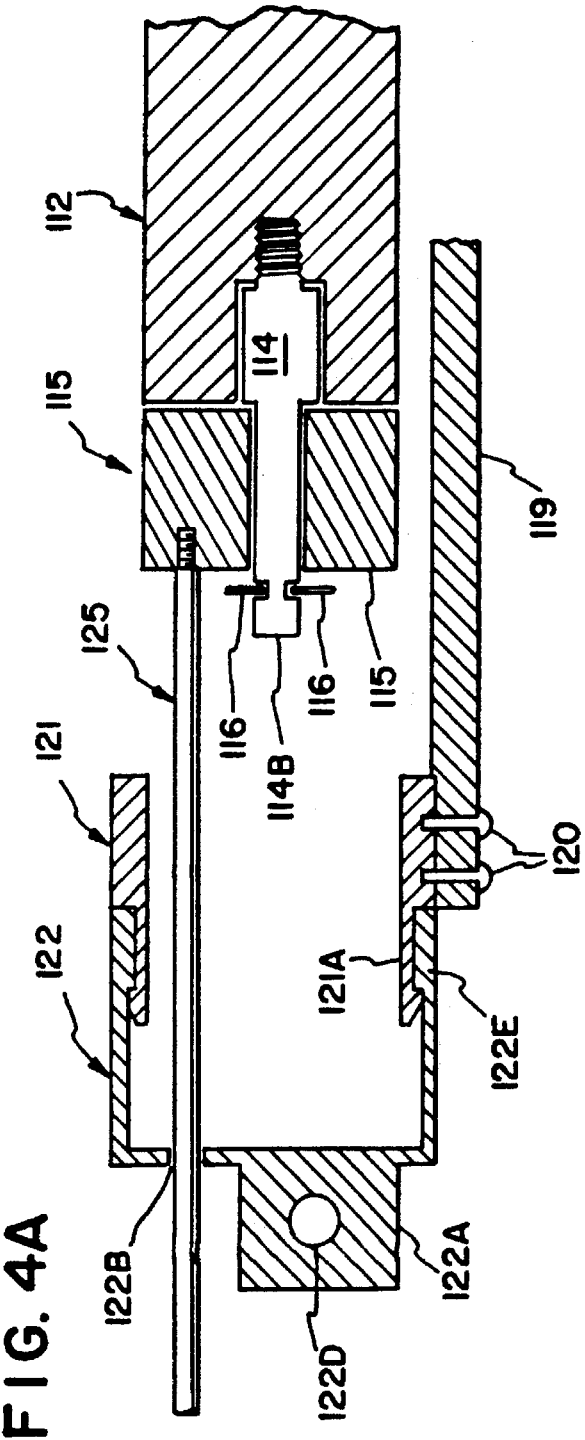
FIG. 4A illustrates a sectional side view of the collar pivot holder, collar pivot support, collar pivot wheel, channel pin holder and channel pivot.

The surgical apparatus described herein includes a frame and handle portion supporting an endoscopic portion, i.e., an extended tube-like portion having a relatively narrow diameter, on the order of about 10 millimeters, for insertion into a small opening in or tube inserted into the body, such as in the abdominal cavity. The endoscopic portion defines a longitudinal axis and has a length appropriate for reaching the operation site in the interior of the body. The apparatus may be used in conjunction with endoscopes (devices for visually examining the interior of the body, for example, by means of fiber optics). The encloseopic portion of the apparatus is inserted through the small opening or wound, manipulated to the operation site, and the instrument is actuated. The encloseopic portion has a fastening and cutting portion including an elongated housing which carries a fastening and cutting portion to the operation site. The fastening and cutting portion includes jaws defined by a staple carrying cartridge (typically located at the distal end of the housing), an anvil and further includes a knife. Actuating the operating portion must be accomplished via intermediate components disposed on or within a narrow longitudinally extending tubular structure. The bulk of the primary operating components are housed on or within a frame, which is located outside the human (or animal) body being operated upon.

The instrument of the present invention has three basic actions or functions.

First, the endoscopic portion is introduced into the body and positioned with the jaws aligned at the stapling site to receive the target tissue. This may involve rotation of the endoscopic portion relative to the body, either by rotating the stapling instrument, as a whole, by rotating the endoscopic portion relative to the frame as permitted in the preferred embodiments, or a combination of both actions.

Second, the instrument has a means for securing the target body tissue between the cartridge assembly and the anvil. This is accomplished by a clamping action. With the target tissue clamped between the anvil and the cartridge assembly, a camming means which surrounds the housing and anvil member is employed to close the jaws of the apparatus and clamp the tissue between the anvil and the tissue contacting surface of the cartridge.

The third action is that of applying the staples to the body tissue. A longitudinally extending channel is employed to deliver longitudinal motion to pusher cam bars and a tissue cutting knife. The cam bars contact pusher elements which drive the staples through the body tissue against the fastener forming or forming surface of the anvil. After the instrument has been fired, the clamping action of the jaws is released and the instrument may be withdrawn from the body. The following details will provide an in-depth understanding of the various elements, operations and functions of the present invention.

FIG. 1 shows a cutaway perspective view of the instrument of the present invention 100, which generally comprises a frame 102 supporting an endoscopic portion 103, means for actuating the instrument to clamp body tissue, and means for firing the instrument to drive staples into the body tissue and form an incision in the tissue between staple rows.

More particularly, referring now to FIGS. 1 and 2, frame 102 has two parts: a left portion 102L and a right portion 102R. These portions are optimally fastened together by means of fastening screws 101, although rivets, welds or other means of joining the two frame parts may also be used. The left portion 102L has a vertical elongated slot 102A to allow access to a thumbwheel 123 (See FIGS. 1 and 4). Frame 102 is elongated and has an interior surface defining a distal opening 102B, proximal opening 102C, an interior distal cylindrical chamber 102D, an interior proximal cylindrical chamber 102E, a circumferential thumbwheel mounting groove 102H, an upper guideway 102F, and a lower guideway 102G. The frame is of an overall size and shape convenient for being held in the hand.

Referring additionally now to FIG. 3, toggle lever 104 transfers motion to the toggle links discussed below and thereby provides a means to activate the clamping action of the apparatus in response to manual pressure from the surgeon or other operator of the instrument. Toggle lever 104 is an elongated piece having a distal end pivotally mounted in proximity to the distal end of the frame by means of lever pivot pin 105, which is disposed through transversely aligned aperture 104B in the distal end of the toggle lever 104. Toggle lever 104 further has a proximal end pivotally connected to toggle link 107 by means of toggle link pin 106 which is disposed through aperture 104A in the toggle lever. In response to pressure, the toggle lever 104 rotates around the axis defined by toggle lever pin 105, and transfers movement to the toggle links.

Toggle link 107 is an elongated member having a rounded first end with fork member 107A, which defines a longitudinal slot 107C, a transversely aligned aperture 107B for receiving toggle link pin 108, and a backstop surface 107D. The rounded second end of toggle link 107 has a transversely aligned aperture 107E for receiving toggle link pin 106. Toggle link 107 transfers movement from the toggle lever to toggle link 109.

Toggle link 109 is an elongated relatively thin, flat piece having a rounded first end with transversely aligned aperture 109A for receiving pin 110, and a partially rounded second end having transversely aligned aperture 109B for receiving toggle link pin 108, and a rotation limiting member 109C.

The first end of toggle link 109 is mounted in slot 111A of the collar moving pivot 111 by means of pin 110 which is disposed through aperture 109A. The second end of toggle link 109 is pivotally mounted in slot 107C in the fork member 107A of toggle link 107 by means of pin 108. Rotation limiter 109C is a flat angular member projecting proximally from the second end of the toggle link 109. The rotation limiter is adapted to abut the corresponding backstop surface 107D in toggle link 107 such that the joint between toggle links 107 and 109 is prevented from further bending in the distal direction. The rotation limiter 109C thus acts as a locking feature, preventing the toggle lever 104 from being depressed, and thereby preventing the clamping function to be actuated. When the coupling is bent in the proximal direction, however, the toggle lever 104 can be fully depressed so as to actuate the apparatus by moving collar moving pivot 111.

Collar moving pivot 111 is a substantially rectangular shaped piece slidably mounted in the upper guideway 102F of the frame 102. Collar moving pivot has a longitudinal slot 111A and a transversely aligned aperture 111B in proximity to the distal end of the collar proving pivot. The slot 111A is for receiving the first end of toggle link 109, and the aperture 111B is for receiving pin 110 for pivotally mounting said toggle link 109. Collar moving pivot 111 has a depending plate 111C, which has a relatively wide spacer portion 111E and transversely aligned aperture 111D for receiving pin 113 (FIG. 4).

Depending portion 111C is mounted in slot 112B of the collar pivot holder 112 (FIG. 4). Pin 113 disposed through aperture 112C in the collar pivot holder and 111D in the collar moving pivot, links these two pieces. Collar moving pivot 111 provides a means to convert the rotational motion of the toggle links to linear movement in the longitudinal direction.

Referring additionally to FIGS. 4 and 4A, collar pivot holder 112 is a substantially cylindrical piece which is located below the collar moving pivot 111, and which is slidably mounted in the proximal cylindrical chamber 102E. Collar pivot holder 112 has a distal end with an internally threaded axial hole 112A, and a proximal end with a longitudinal slot 112B for receiving depending plate 111C of the collar moving pivot, and transverse aperture 112C adapted to receive pin 113 for mounting the depending plate 111C.

Collar pivot holder 112 provides a means to transmit longitudinal movement from the collar moving pivot to the collar pivot wheel 115, which is connected by means of the collar pivot support 114.

Collar pivot support 114 has a longitudinally projecting threaded bolt portion 114A at its proximal end for mounting into the hole 112A of the collar pivot holder 112. At its distal end, collar pivot support has a longitudinally projecting pin 114B with a circumferential notch 114C for engaging E-ring retainer 116. Pin 114 is disposed through axial aperture 115A of the collar pivot wheel 115, and the distal end of the pin with notch 114C projects out through the distal end of said aperture 115A where E-ring retainer 116 is clipped onto said notch thereby maintaining collar pivot wheel 115 on pin 114B. Collar pivot support 114 not only provides a means for connecting collar pivot wheel 115 and collar pivot holder 112 so that longitudinal motion may be transferred, but also provides an axis (pin 114B) around which collar pivot wheel 115 may freely rotate.

Collar pivot wheel 115 is a substantially cylindrical piece slidably mounted in the proximal cylindrical chamber 102E of body 102. Concentric aperture 115A extends from the proximal to distal end of said collar pivot wheel for receiving pin 114B. Collar pivot wheel 115 further has eccentric hole 115B in its distal end for receiving mounting bolt 125A of the collar shaft 125 (FIG. 6). Collar pivot wheel 115 is movable both longitudinally within proximal cylindrical chamber 102E, and rotationally around pin 114B. Collar pivot wheel 115 transfers longitudinal motion to the collar shaft 125 for the purpose of clamping the jaws of the apparatus.

Channel pin holder 121 is a substantially cylindrical shaped piece slidably mounted in the distal cylindrical chamber 102D, and having a hollow axial interior. At its distal end, channel pin holder has a male snap-in plug 121A with contraction slots 121B for mounting into the proximal end of channel pivot 122. Channel pin holder 121 is mountable by means of screws 120 onto firing support shaft 119 and provides a means for transferring longitudinally movement from the firing support shaft 119 to the channel pivot for the purpose of firing the surgical fasteners. Channel pin holder 121 moves only longitudinally. The snap-in plug 121A serves as an axis around which the channel pivot 122 may rotate.

Firing support shaft 119 is an elongated substantially rectangular piece slidably mounted in the lower guideway 102G. Concave surface portion 119A at the distal end of the firing support shaft 119 is for mounting the channel pin holder 121, and has a curvature corresponding to the outside surface of the channel pin holder 121. Screws 120 are disposed through transverse apertures 119C in the firing support shaft 119, and into holes in the bottom of channel pin holder 121 for mounting said channel pin holder 121 to the firing support shaft 119. At its proximal end, firing support shaft 119 has a longitudinally extending threaded hole 119B for receiving threaded screw portion 118A of the plunger 118.

Firing support shaft transfers longitudinal movement from the plunger 118 to the channel pin holder 121 for firing the fasteners.

Plunger 118 is a rod having threaded screw mounting portions at both the distal and proximal ends. The distal screw portion 118A is for mounting to the threaded hole 119B in the firing support shaft 119. The proximal screw portion 118B is for mounting a push button 117 by means of central threaded aperture 117A in the push button. The plunger rod extends proximally outside the proximal opening 102C in the body 102.

Figure 8:
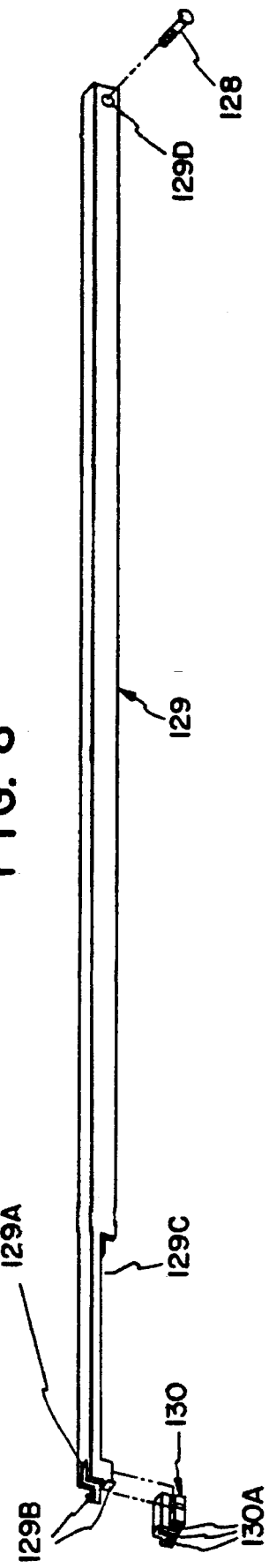
FIGS. 8 and 9 illustrate the cam bar channel, cam bars, knife and cam bar adapter.

Channel pivot 122 is a substantially cylindrical piece located within the distal cylindrical chamber 102D of frame 102. At its proximal end, channel pivot 122 has opening 122C to serve as a receptacle for snap-in portion 121A of the collar pin holder 121 upon which the channel pivot 122 is rotatably mounted. As can be seen from FIG. 4A, receptacle portion 122C has a circumferential lip 122E to interlock with the snap-in portion 121A. At its distal end channel pivot 122 has a stud 122A for mounting the proximal end of cam bar channel 129 (FIG. 8). Mounting screw 128 is disposed through transverse aperture 122D to secure the cam bar channel 129. Collar shaft 125 is disposed through aperture 122B.

Channel pivot 122 provides a means for transferring longitudinal movement from the channel pin holder 122 to the cam bar channel 129 for the purpose of firing the surgical fasteners. Channel pivot 122 also provides a means to rotate the cam bar channel 129 and collar shaft 125 around the longitudinal axis of the instrument.

Thumbwheel 123 is disk shaped piece rotatably mounted in the circumferential thumbwheel mounting notch 102H. Thumbwheel 123 has a distally extending cylindrical projection 123B, rectangular slot 123A, detents 123C transverse to slot 123A, projecting distally from the cylindrical projection 123B, and a circumferential surface 123D which partially projects through elongated notch 102A. Thumbwheel 123 can be rotated by manually applying a turning force to the portion of the circumferential surface 123D which projects through the elongated notch. Upon being rotated thumbwheel 123 will thereupon turn the cover, cam bar channel, collar shaft, around the longitudinal axis of the instrument for the purpose of imparting rotation to the endoscopic portion of the apparatus distal to the frame.

Figure 5:
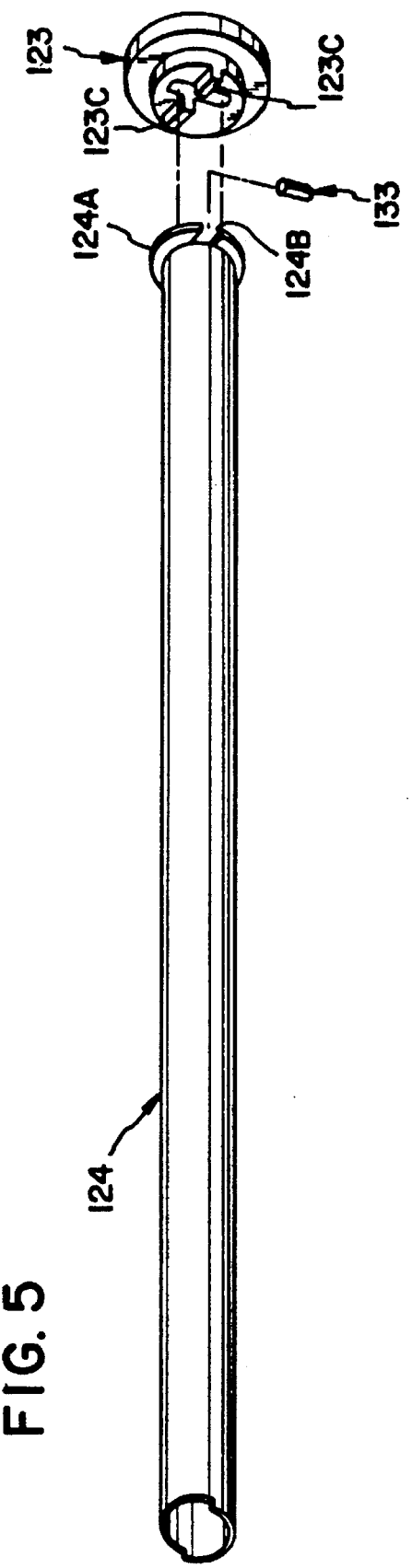
FIG. 5 shows the tubular cover.
Figure 5A:
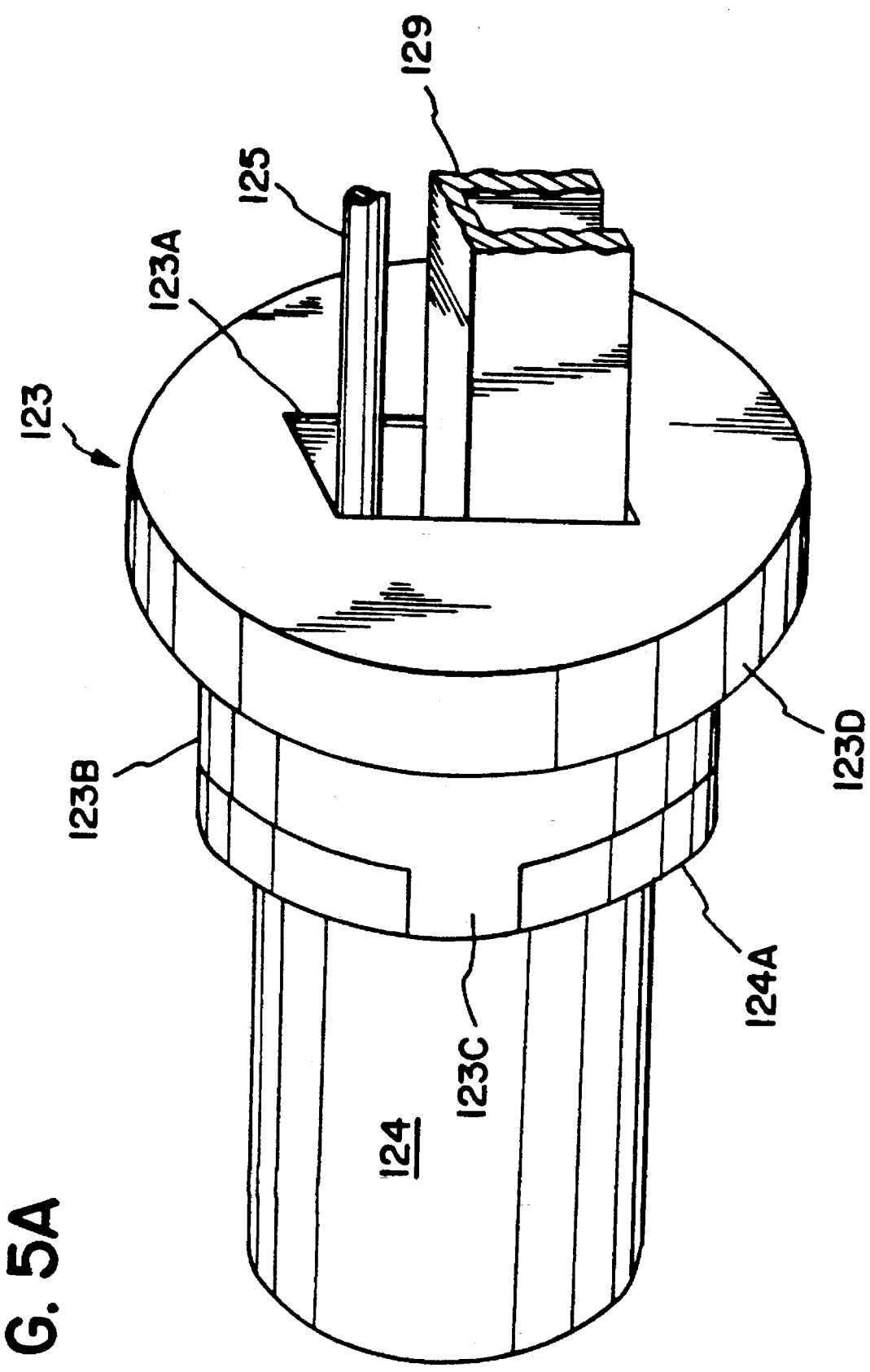
FIG. 5A illustrates the connection between the cover and thumbwheel.

Referring additionally now to FIGS. 5 and 5A, cover 124 is a relatively long tubular piece having a diameter appropriate for use in endoscopic surgical procedures and projecting distally through the distal opening 102B of the frame in alignment with the longitudinal axis of the instrument. At its proximal end, cover 124 has a flange 124A which has notches 124B to cooperatively engage detents 123C of the thumbwheel 123. Flange 124A is mounted flush against cylindrical projection 123B of the thumbwheel. Cover 124 is rotatably mounted as to turn in conjunction with the rotation of the thumbwheel. Collar shaft 125 and cam bar channel 129 extend longitudinally through the interior of the cover 124. Cover 124 provides a means for enclosing the collar shaft 125 and cam bar channel 129 to prevent them from contacting extraneous body tissue while the instrument is being used.

Referring additionally to FIGS. 6 and 7, collar shaft 125 is a relatively long rod in parallel alignment with the longitudinal axis of the instrument and having a proximal end with a threaded screw portion 125A for mounting to the collar pivot wheel 115, as discussed above, and a distal end with a screw portion 125B for mounting to the tapped hole 126A in collar plug 126. Via collar plug 126, collar shaft 125 transmits longitudinal motion to the collar 124 for the purpose of closing the jaws of the instrument to secure the target body tissue. Collar shaft 125 moves longitudinally, and it may be turned around the instrument axis although it does not rotate relative to its own axis.

Collar plug 126 provides a means for connecting collar shaft 125 to collar 127. Collar plug 126 has a threaded aperture 126A for mounting screw portion 125B of the collar shaft 125, and distal radial projections 126 which mount in circumferential slots 127A in the collar 127.

Collar 127 is a substantially tubular piece located distally to the cover 124 and aligned with the longitudinal axis of the instrument. Collar 127 has circumferential slots 127A in proximity to the proximal end of the collar 127, and a distal camming edge 127B. As seen in FIG. 15A, distal camming edge 127B provides a means for closing the jaws of the instrument to secure the target body tissue. This is discussed in more detail below.

Referring additionally now to FIG. 8, cam bar channel 129 is an elongated piece having an inverted U-shaped cross section and which is slidably mounted in housing 134. At its proximal end, cam bar channel 129 has a transverse aperture 129D for receiving fastening screw 128. The proximal end of the cam bar channel 129 is mounted to the rectangular mounting stud 122A of channel pivot 122 (FIG. 4). At its distal end, cam bar channel 129 has a gripping fork 129B and slot 129A. Gripping fork 129B and slot 129A provide a means of engaging and holding cam bar adapter 130. Longitudinal notches 129C allow the cam bar channel to move without interference from anvil pivot pin 135 (FIG. 11), as discussed below. Cam bar channel 129 transmits longitudinal motion from channel pivot 122 to the cam bars 131 and knife 132 for performing the tissue fastening operation.

Figure 9:
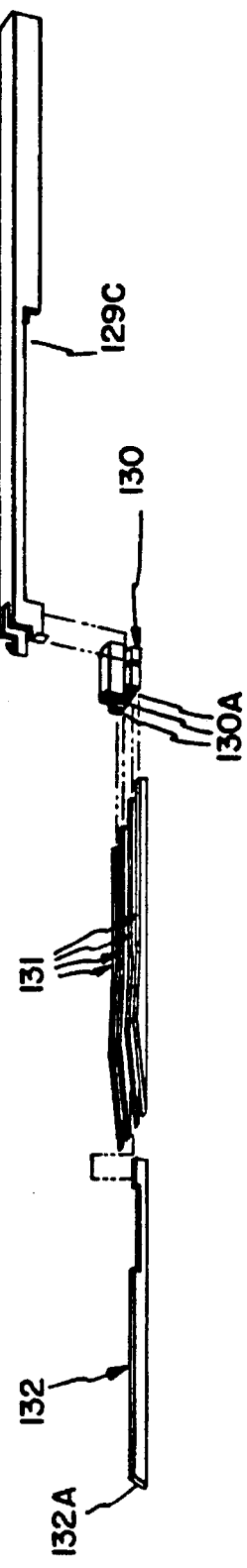

Referring to FIGS. 8 and 9, cam bar adapter 130 is mounted to the gripping fork 129B of the cam bar channel 129 and provides a means for holding the cam bars 131 and knife 132. Cam bars 131 are parallelly and longitudinally aligned. Their proximal ends are mounted in the longitudinal slots 130A of cam bar adapter 130. Knife 132, parallelly and longitudinally aligned with cam bars 131, is also mounted to a slot 130A in the cam bar adapter 130. Knife 132 has a cutting edge 132A on its distal end.

Figure 11A:
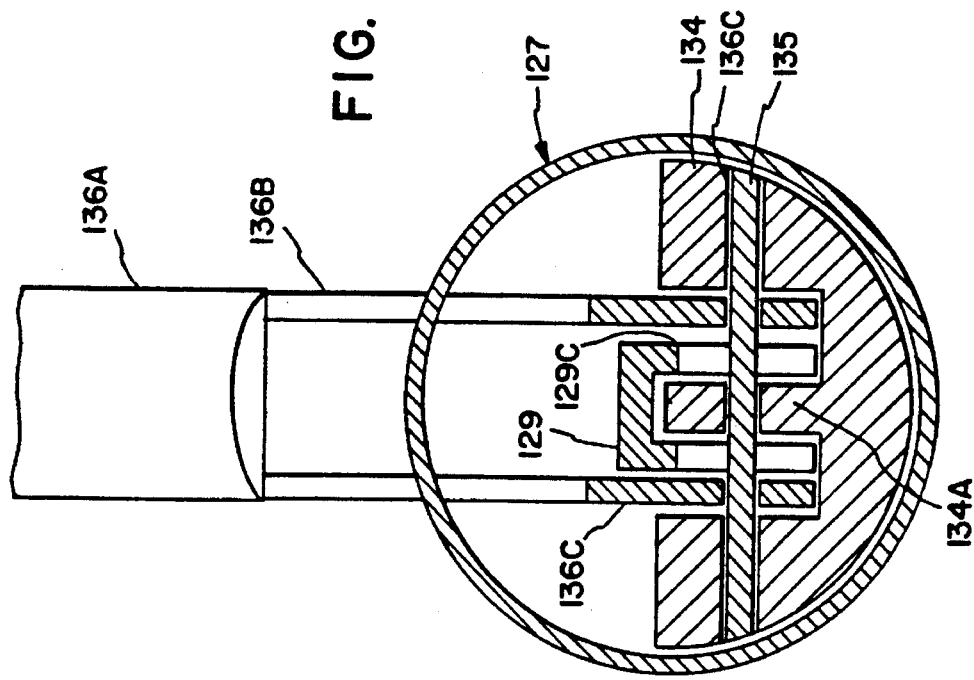
FIG. 11A illustrates a sectional view of the housing and collar.

Referring additionally now to FIGS. 10, 11, and 11A housing 134 is an elongated piece which is aligned with the longitudinal axis of the instrument. Housing 134 has a proximal end mounted to the cylindrical projection 123B of thumbwheel 123 by means of pin 133 (FIG. 5). At its distal end, housing 134 has a relatively wider section 134B for engaging and holding a cartridge assembly 137. Transverse aperture 134C receives anvil pivot pin 135. Housing 134 also has a longitudinally extending center guide rail 134A around which cam bar channel 129 is slidably mounted.

Anvil member 136 is an elongated piece which is pivotally mounted to the housing 134. At its distal end anvil member 136 has an anvil plate 136A with a tissue contacting surface 136E with staple forming depressions 136D (see FIG. 13). Anvil member 136 comprises arms 136B and, at the proximal end, a hinge 136C for pivotal mounting to housing 134 by means of anvil pivot pin 135 disposed through the hinge 136C and aperture 134C. Anvil member 136 is rotatable between an open position (see FIG. 15A) and a closed position (see FIG. 15B) where the anvil forming surface is brought into close cooperative alignment with the cartridge assembly 137. Anvil plate 136A also has a longitudinal center groove 136F to permit passage of knife 132. Anvil member 136 provides one of the jaws of the instrument for clamping and securing the body tissue to be fastened. Preferably, anvil 136 is provided with one or more tissue stops 140 which engage corresponding depressions, openings or indentations in housing 134 (see FIGS. 11, 15A). Tissue stops 140 help prevent over-insertion of tissue into the jaws.

Figure 12:
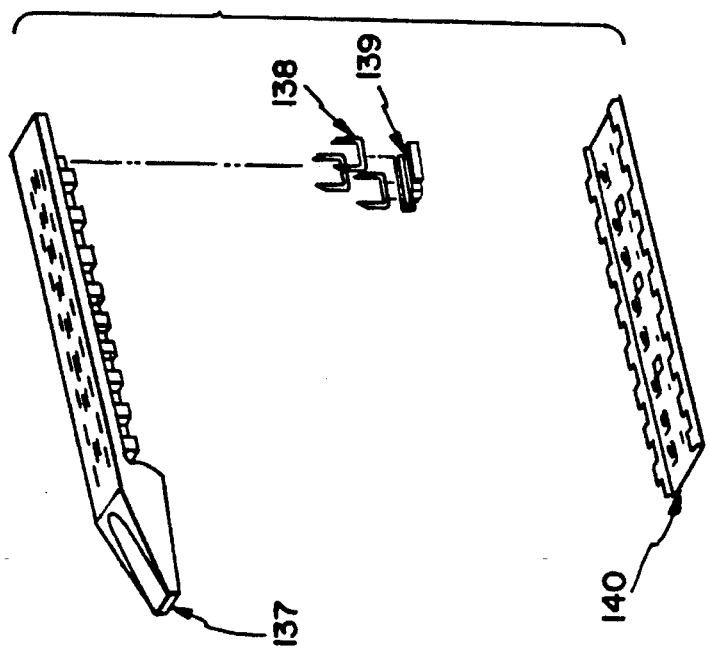
FIG. 12 illustrates an exploded view of the cartridge, staple drive member and staples.
Figure 13:
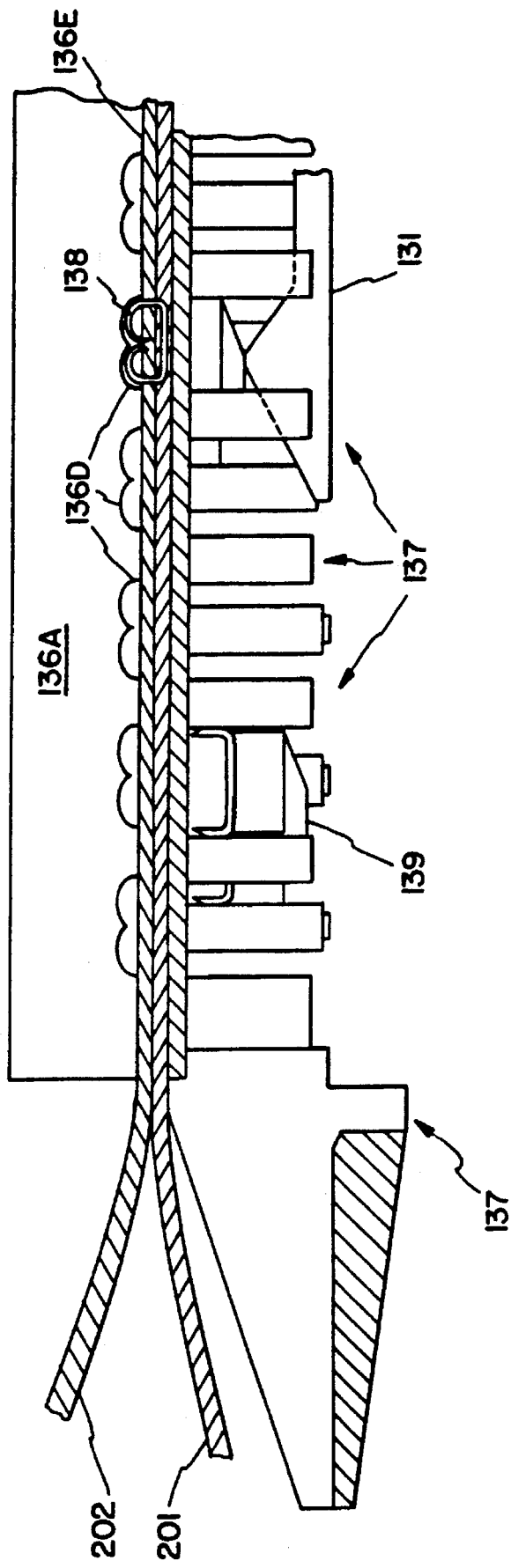
FIG. 13 illustrates a side view of the cartridge.
Figure 14:
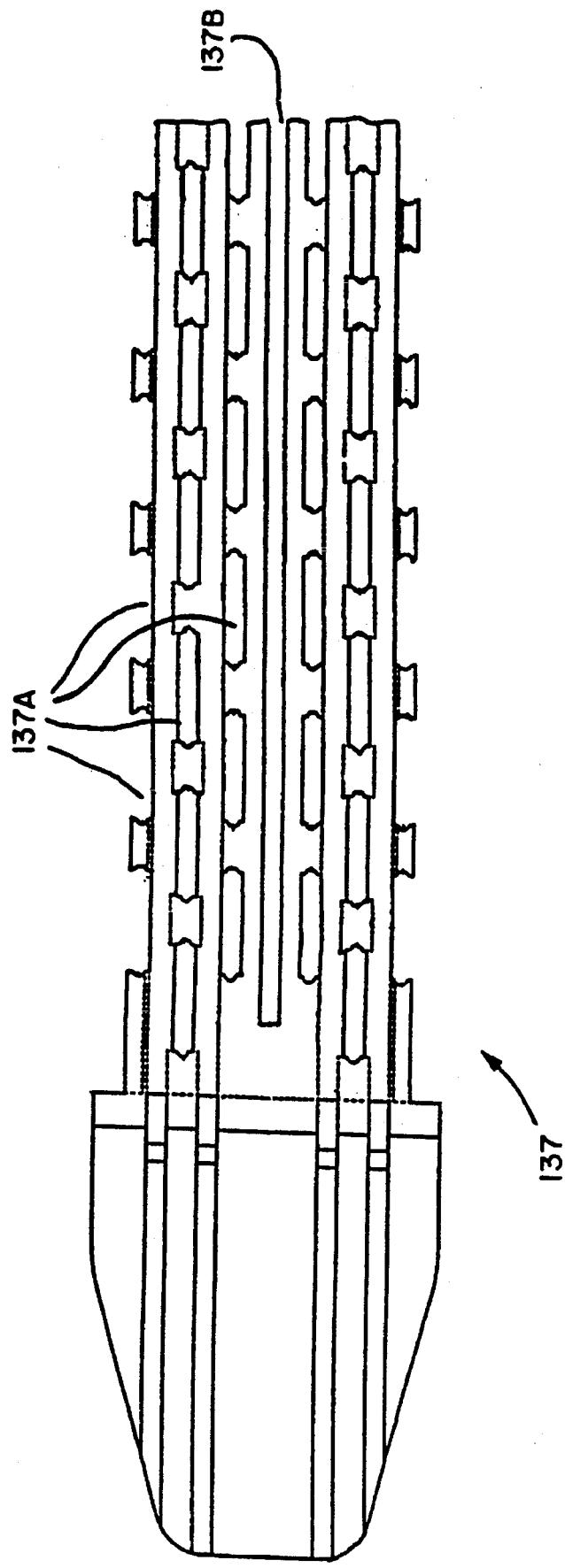
FIG. 14 illustrates the surface of the cartridge which comes in contact with body tissue.
Figure 16:
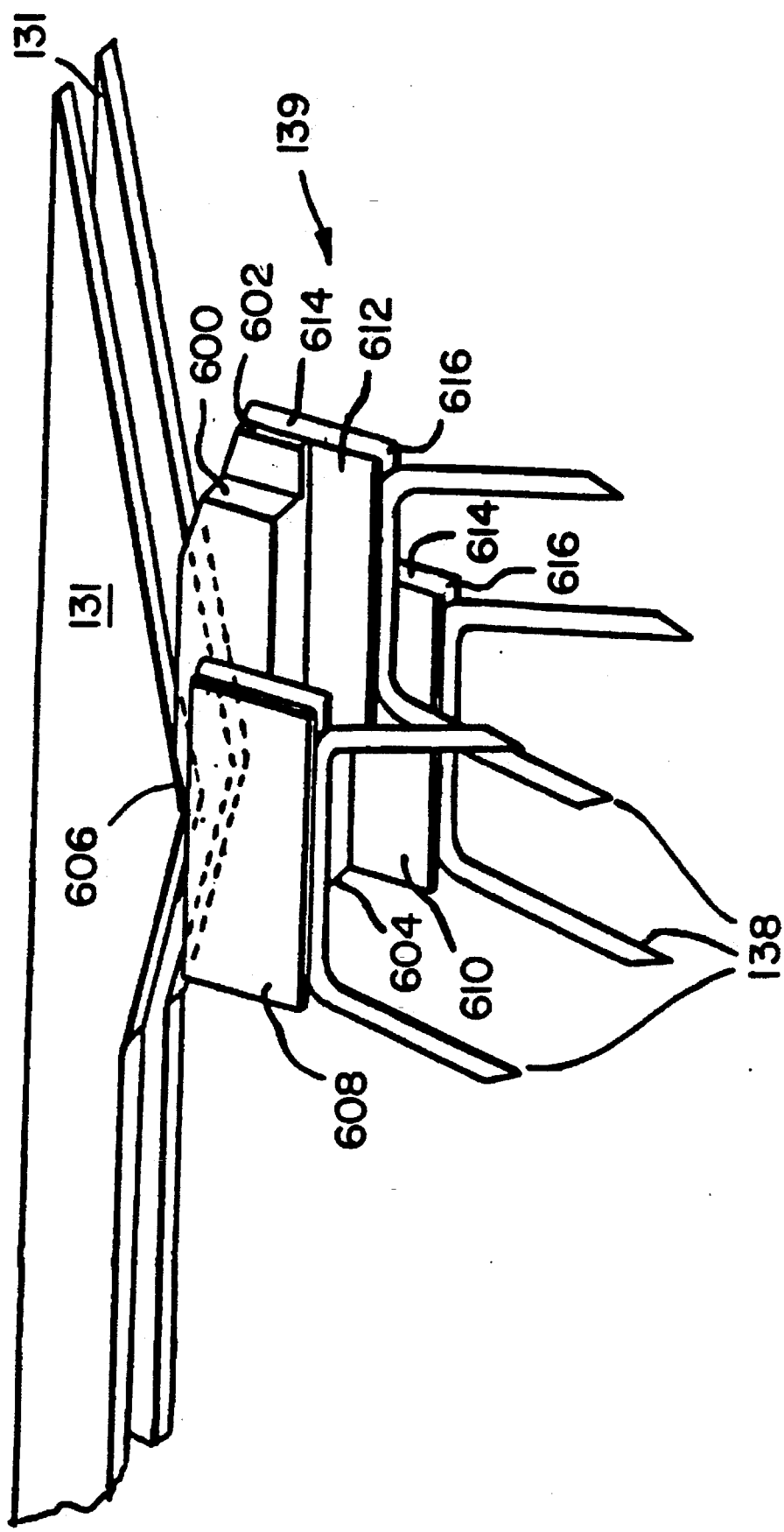
FIG. 16 illustrates a three staple drive member that can be used with the present invention.

Referring additionally now to FIGS. 12, 13 and 14, the cartridge assembly comprises a cartridge 137 with alignment plate 140, pusher elements or staple drivers 139, and surgical fasteners or staples 138. The staples 138 and pushers 139 are disposed within grooved slots 137A such that as the cam bars 131 move distally and longitudinally through the cartridge 137, pushers 139 are driven up through the grooved slots 137A driving staples 138 through the body tissue layers 201 and 202 which are to be joined, and into anvil plate 136A where the legs of the staples are crimped in staple forming depressions 136D. Alignment plate 140 serves as a cover to keep the staple drivers aligned within cartridge 137. Preferably, cartridge 137 contains two rows of staple pusher elements, with each staple pusher element acting on three staples. One such staple pusher element 139 is illustrated in FIG. 16. The preferred staple drive member there illustrated includes a body portion 600 having a distal end 602, a proximal end 604 with at least one camming surface 606, and three substantially rectangular pusher plates 608, 610, 612 aligned in the direction of cam motion. Pusher plates 608, 610 are laterally aligned on either side of body portion 600 and have an end coterminous with the body portion proximal end 604. The middle pusher plate 612 has an end coterminous with the body portion distal end 602. None of the pusher plates extend the full length of the body portion. Preferably, each pusher plate also includes guide rails 614 and a staple cradling notch 616. Guide rails 614 are received by and slide in corresponding slot portions of the cartridge. As shown in FIG. 16, each staple drive member is preferably driven by a double cam bar.

FIG. 14 illustrates the surface of the cartridge 137 which comes in contact with body tissue. Grooved slots 137A terminate in openings through which the staples 138 are ejected. Groove 137B guides the movement of knife 132 through the cartridge.

As will be appreciated from the layout of slots or grooves 137A shown in FIG. 14, the preferred arrangement including two rows of staple drive members, each acting on three staples, results in six rows of staples with three overlapping staggered staple rows on each side of knife groove 137B. Placing three staggered overlapping rows of staples on either side of the incision obtains improved tissue holding strength and hemostasis.

A first alternative embodiment of the invention is illustrated in FIGS. 17–31. In the embodiment there shown the endoscopic portion 300 of the instrument is detachable from the frame and handle portion 301 of the instrument (see FIGS. 17 and 24). Endoscopic portion 300 preferably constitutes a disposable unit, the frame and handle portion of the instrument being reusable with replacement endoscopic portions.

Figure 17:
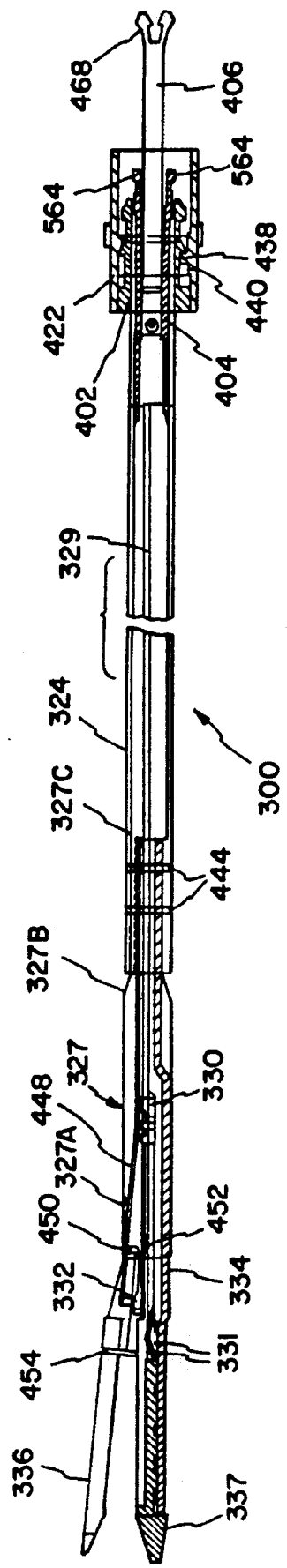
FIG. 17 illustrates a sectional view of the endoscopic portion of the instrument in accordance with a first alternative embodiment of the invention.

Referring now to FIG. 17, a sectional side view of endoscopic portion 300, the endoscopic portion has a housing 324 mounted at the proximal end to a collet 402. At the distal end of the endoscopic portion, housing 324 supports a cartridge housing 334 and an anvil 336. In this embodiment, a clamping tube 327 has a clamping portion 327A of substantially the same outer diameter as housing 324, a tapered section 327B, and a shaft portion 327C having a narrow diameter configured and dimensioned to slide axially within housing 324. The proximal end of the narrow diameter shaft section 327C is fixedly mounted to a clamp tube snap 404. A cartridge 337 is mounted to cartridge housing 334 and engages cam bars 331 and a knife 332. As shown in FIG. 17, cam bars 331 preferably are staggered longitudinally relative to one another in order to improve the balance of forces generated in driving the preferred three staple drive members to eject three staggered parallel rows of staples on either side of the incision formed by knife 332. Similar to the first described embodiment, cam bars 331 and knife 332 engage and are supported by a cam bar adapter 330 which, in turn, engages the distal end of a cam bar channel 329. The proximal end of cam bar channel 329 is fixedly mounted to a channel adaptor 406.

Figure 18:
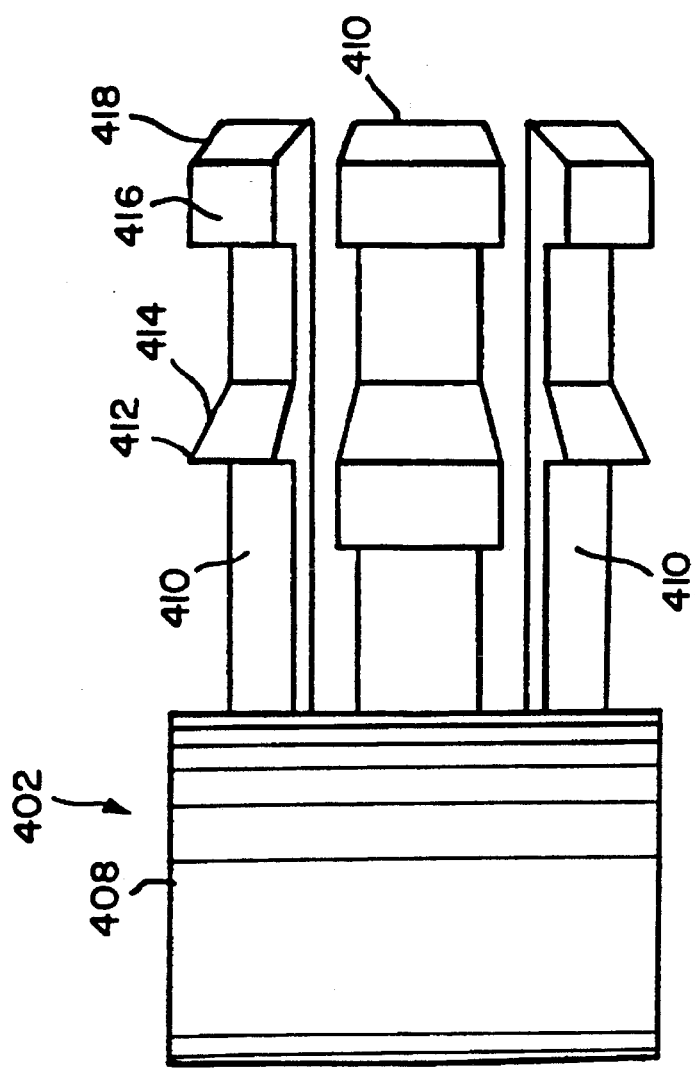
FIG. 18 illustrates a side view of the collet in accordance with the first alternative embodiment of the invention.

As shown in FIG. 18, collet 402 is substantially cylindrical in shape having a cylindrical support section 408 at the distal end thereof and a plurality of collet fingers 410 extending longitudinally in the proximal direction. Each collet finger 410 has an outwardly projecting midsection portion 412 with an inclined surface 414 projecting axially inward in the proximal direction. Each collet finger also has an outwardly projecting proximal flange portion 416 terminating at an inclined surface 418 extending axially inward in the proximal direction.

Figure 19:
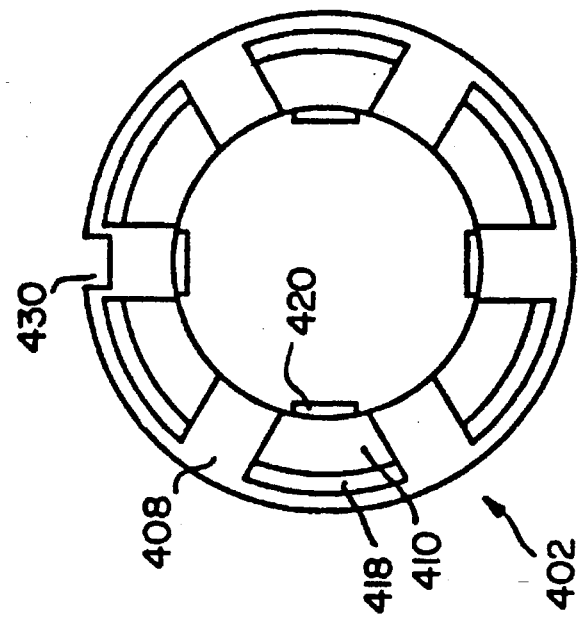
FIG. 19 illustrates is a proximal end view of the collet of FIG. 18.

FIG. 19 is a proximal end view of collet 402, illustrating six collet fingers 410 configured as sections of a cylinder. Collet 402 and, more specifically, collet fingers 410 are preferably made of plastic and may be flexed inwardly from their normal, or rest position. Fingers 410 have memory and return to their rest position when the flexing force is released.

The inner diameter of cylindrical support section 408 is configured to accept the proximal end of housing 324. The proximal end of housing 324 is fixed to cylindrical support section 408 by any appropriate means, including but not limited to friction fit and/or engagement of one or more projections or ribs 420 on the inner surface of cylindrical support section 408 (see FIG., 19) with corresponding openings or slots on the housing 324.

Referring again to FIG. 17, collet 402 is disposed within and engages an outer sleeve 422 such that sleeve 422 is rotationally immovable relative to the collet but is longitudinally movable relative to the collet with a limited range of motion. As shown more particularly in FIG. 20, sleeve 422 has an outer gripping surface including a gripping ring 424. Sleeve 422 has a distal portion 426 including an inwardly extending longitudinal rib 428 which engages a longitudinal slot 430 on the outer surface of the collet cylindrical support section 408 (see FIG. 19). As will be apparent, engagement of rib 428 and slot 430 prevents rotational movement of the sleeve 422 relative to the collet and vice versa. Sleeve 422 also has an inwardly projecting flange 432 at the sleeve midsection. Flange 432 has an area 434 of minimum diameter which corresponds to and engages the outer diameter surface of collet fingers 408 between outwardly projecting flanges 412, 416 (see FIG. 17). Flange 432 also has an inclined surface 436 projecting axially inward in the proximal direction. Inclined surface 436 substantially corresponds to and engages inclined surface 414 on collet fingers 410 (see FIGS. 17 and 18). In order to limit the range of longitudinal motion of sleeve 422 relative to collet 402, proximal and distal limiting stops 438, 440 are provided. Proximal limiting stop 438 engages the distal flat surface of the outwardly projecting midsection 412 of one or more collet fingers 410, thereby limiting longitudinal motion of the sleeve in the proximal direction. Distal limiting step 440 abuts the proximal flat surface of collet cylindrical support section 408, thereby limiting the longitudinal motion of the sleeve in the distal direction.

Between these two extreme positions, limited longitudinal motion of the sleeve in the distal direction from the position illustrated in FIG. 17 is permitted, such that inclined surfaces 414, 436 exert axially inward force on collet fingers 410. In this manner, collet fingers 410 and, more particularly, the proximal ends of collet fingers 410, may be flexed inwardly from their rest or memory position for reasons to be discussed hereinafter.

The proximal section 442 of sleeve 422 has an inner diameter which is configured and dimensioned to accept and surround a corresponding outer tube projection on the frame with unencumbered rotational motion between the sleeve and the frame.

Referring again to FIG. 17, radial housing support pins 444 extend through the cylindrical interior of housing 324 near the distal end thereof. Pins 444 extend through longitudinal slots 446 on clamping tube 327 (see FIG. 21) and a similar slot in channel 329 (not shown). The proximal end of cartridge housing 334 is fixedly mounted to housing 324 by housing support pins 444. At the distal end, cartridge housing 334 supports cartridge 337. Housing support pins 444 also affix the proximal end of an anvil leaf spring 448 to housing 324. The distal end of spring 448 supports anvil 336. As shown in FIG. 17, anvil spring 448 acts as a leaf spring to bias the anvil into the open position there shown.

Preferably, at least one pair of corresponding anvil alignment guides, shown as alignment pin and slot 450, 452, are provided on the anvil and cartridge. Alignment guides 450, 452 ensure proper alignment of the anvil and cartridge tissue contacting surfaces so that staples ejected from the cartridge accurately engage corresponding staple forming grooves in the anvil. Also preferred are one or more tissue stops 454 to ensure proper placement of the body tissue between the jaws without over-insertion of the tissue beyond the tissue contacting surfaces of the anvil and cartridge.

Clamp tube 327 surrounds the proximal portion of the anvil, anvil spring and cartridge housing in a manner similar to the first described embodiment, and moves longitudinally between the open position shown in FIG. 17 to a distal, closed position clamping the upper jaw closed against the lower jaw (see FIGS. 15A and 15B). In the latter position body tissue is clamped between the anvil and cartridge in the manner illustrated in FIG. 13.

Figure 21:
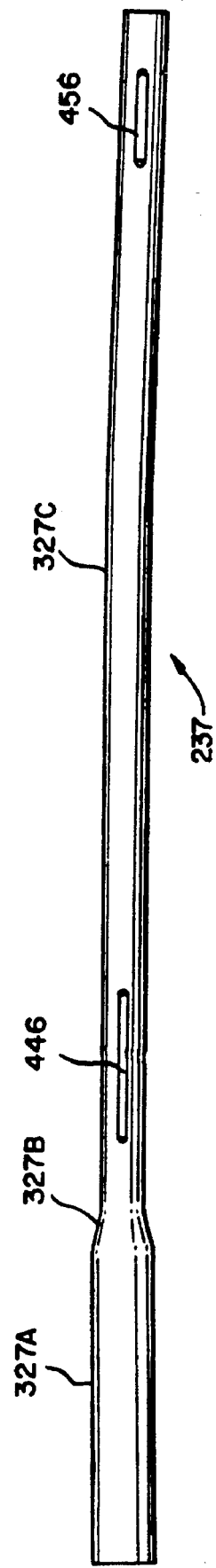
FIG. 21 illustrates a top plan view of the clamp tube of the first alternative embodiment of the invention.

As shown in FIGS. 17 and 21, clamp tube 327 has a clamping portion 327A with an outer diameter substantially the same as housing 324. At the proximal end of clamping portion 327A clamp tube 327 has a tapered section 327B which joins clamping portion 327A to narrow diameter shaft portion 327C. Clamping portion 327A and shaft portion 327C are substantially cylindrical. Shaft portion 327C has an outer diameter smaller than the inner diameter of cylindrical housing 324, thereby permitting longitudinal movement of the clamping tube relative to the housing. As shown in FIG. 21, shaft portion 327C includes longitudinal slots 446, 456. As previously described, housing support pins 444 extend through slots 446. It will be noted that slots 446 are configured to permit sufficient longitudinal movement of clamp tube 327 and channel 329 relative to housing 324 to close the instrument jaws and fire the instrument. Pins 444 isolate the anvil and cartridge housing assemblies relative to housing 324, and prevent longitudinal or rotational movement of the anvil or cartridge assemblies relative to the housing. Pins 444 also prevent rotational movement of the collar tube or channel tube relative to housing 324.

Figure 22:
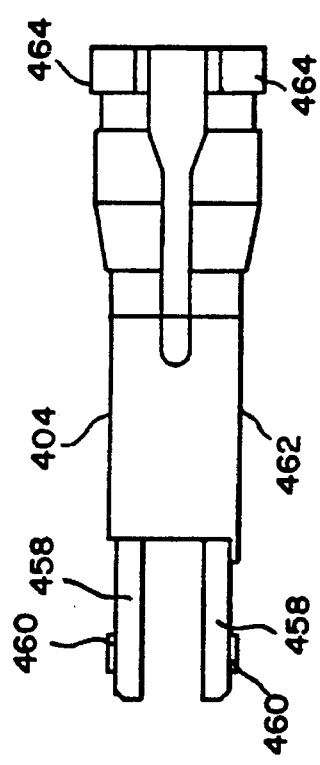
FIG. 22 illustrates a top plan view of the clamp tube snap of the first alternative embodiment of the invention.

The proximal end of clamp tube 327 is connected to the distal end of clamp tube snap 404 (see FIGS. 17 and 22). As shown in FIG. 22, clamp tube snap 404 includes two distal legs 458 which extend into the proximal end of clamp tube 324. Outwardly extending pins 460 isolate clamp tube 324 and clamp tube snap 404 relative to one another. Clamp tube snap 404 further includes a substantially cylindrical midsection 462 and clamp snap fingers 464. It will further be appreciated that inward deflection of collet fingers 410 by distal movement of sleeve 422 also inwardly deflects clamp snap fingers 464 from their rest position shown in FIG. 17.

Channel 329 is disposed within clamp tube 327 and is longitudinally movable therein for imparting longitudinal motion to cams 331 and knife 332. Referring to FIGS. 17 and 23, the proximal end of channel 329 is fixed to the distal end of channel adaptor 406, such as by tabs 466 on channel adaptor 406 engaging corresponding slots on channel 329 (not shown). The shaft of channel adaptor 406 extends longitudinally through the center of clamp tube snap 404 and terminates with a female snap-in receptor defined by prongs 468.

The preferred frame for this embodiment is shown in FIGS. 24-31.

Figure 24:
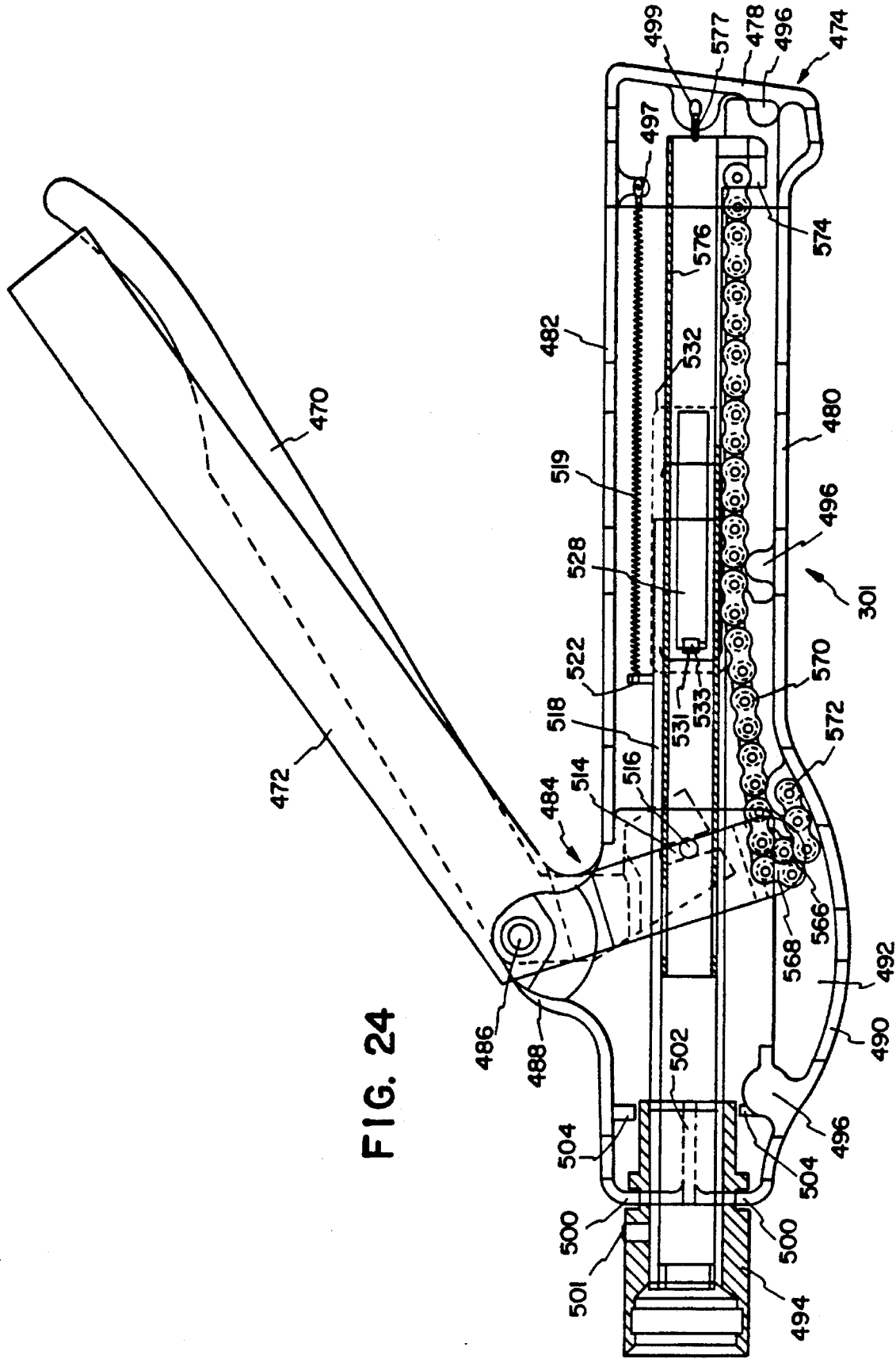
FIG. 24 illustrates a sectional side view of a handle and frame portion in accordance with the first alternative embodiment.
Figure 25A:
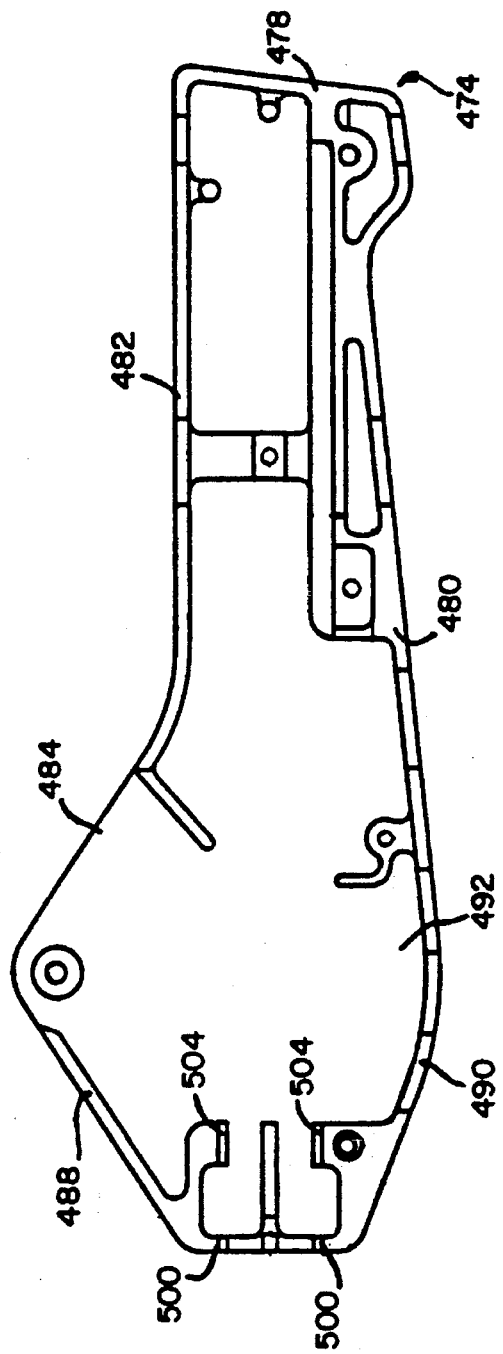
FIG. 25A illustrates a sectional view of the frame in accordance with the first alternative embodiment.
Figure 25B:
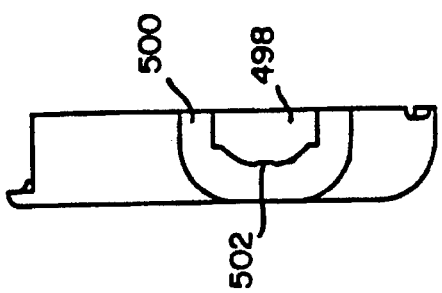
FIG. 25B illustrates a distal end view of the frame half illustrated in FIG. 25A.

As shown in FIGS. 24, 25A and 25B, the frame and handle assembly in this embodiment is configured with a double handle. In this embodiment, inner handle 470 controls the tissue clamping action of the instrument jaws, and outer handle 472 controls firing of the instrument. Frame 474, which may be molded and/or machined in whole or in part, is substantially rectangular with a closed proximal end 478, a lower gripping surface 480 and an upper, handle receiving surface 482. An opening 484 is provided to receive handles 470, 472 mounted to hinge pin 486. Handles 470, 472 may be biased in the open position, illustrated in FIG. 24, as by spring loading. The distal portion of opening 484 is defined by an upwardly extending lip 488. The lower surface of the frame includes a protruding bulbous region 490 distal to gripping surface 480. As explained in greater detail below, bulbous region 490 defines an interior cavity 492 sufficient to permit arcuate travel of the handles. The distal end of frame 474 terminates at a substantially flat surface having a distal opening 498 (see FIG. 25B). Preferably, frame 474 is cast and/or machined in two left and right halves fastened together by screws or rivets 496, 497, 499. Each frame half includes a distal inwardly projecting flange 500 and a longitudinal rib 502 which define distal opening 498 (see FIG. 25B). Inwardly projecting flange 500, in conjunction with the exterior walls of frame 474 and interior walls 504, define a distal frame chamber 506 to receive and support the proximal end elf an outer tube 494.

Figure 26A:
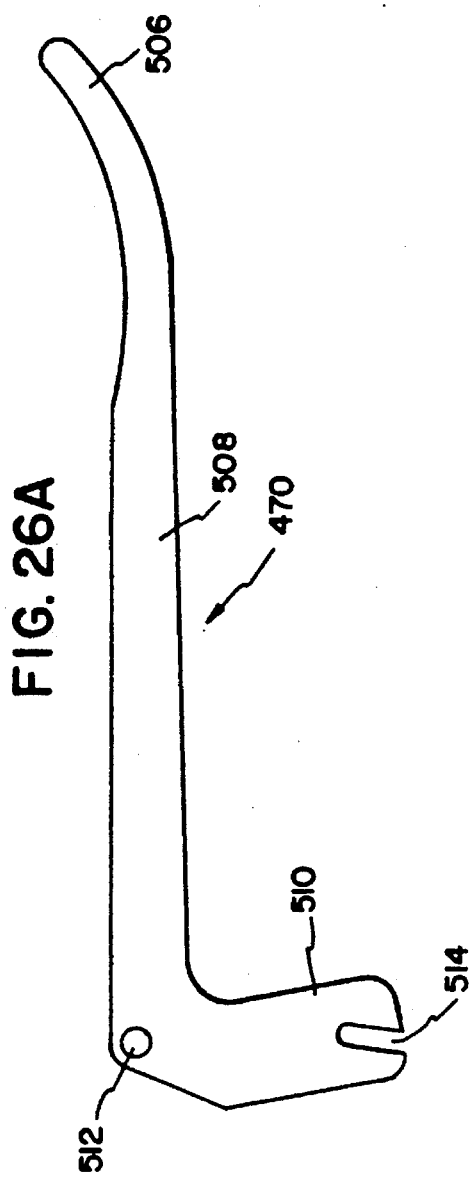
FIGS. 26A and 26B illustrate side and distal end views, respectively, of the inner handle of the first alternative embodiment.
Figure 26B:
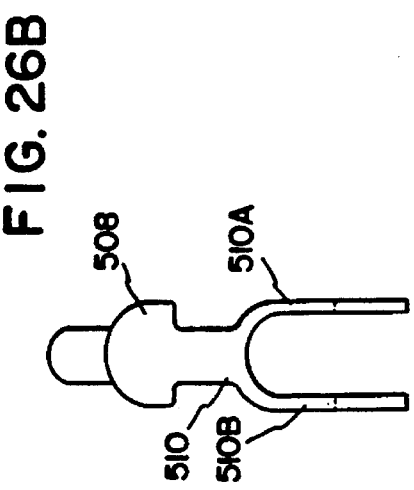

Referring now to FIGS. 24, 26A and 26B, inner handle 470 includes a gripping tab portion 506 at the proximal end of an inner handle arm 508 and a lever arm portion 510. A hinge pin aperture 512 is provided at the distal end of arm 508 to receive hinge pin 486, such that inner handle 470 rotates about hinge pin 486 to obtain leveraging mechanical advantage at lever arm 510. As shown in FIG. 26B, a distal end view of the inner handle, lever arm portion is formed in a substantially U-shaped configuration with a pair of lever arm forks 510A, 510B. Referring again to FIG. 26A, each leveraging fork includes an elongated slot 314 for receiving frame clamp tube pins 516 projecting from either side of a frame clamp tube 518 straddled by lever arm forks 510A, 510B.

Figure 27E:
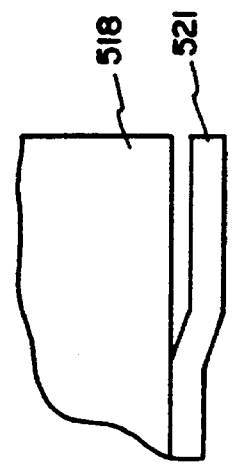
FIGS. 27A, 27B, 27C, 27D and 27E illustrate bottom plan, front side, sectional front side and two partial rear side views, respectively, of the frame clamp tube.
Figure 27D:
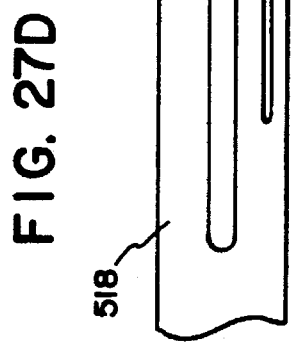
Figure 27A:
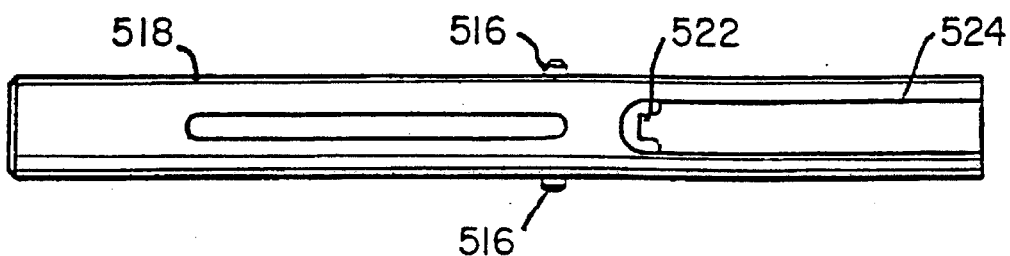
Figure 27B:
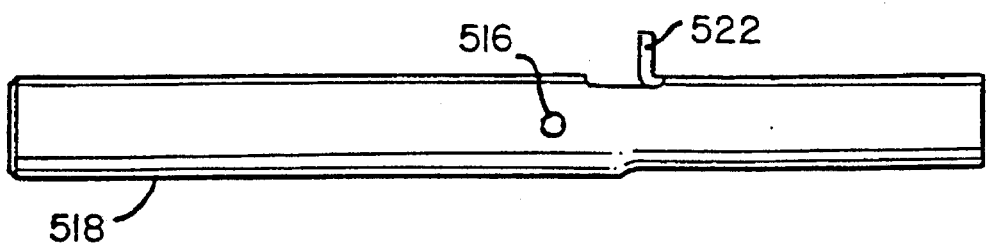

Frame clamp tube 518 is best described by reference to FIGS. 27A through 27E. FIG. 27A is a bottom view of frame clamp tube 518 showing clamp tube pins 516 projecting outwardly to either side to engage slots 514 on the inner handle lever arm portion. An elongated U-shaped slot 524 is provided for reasons explained later. As shown in FIG. 27B, a front side view of tube 518, a spring retaining pin 522 is formed and protrudes outwardly from the frame clamp tube.

Figure 27C:
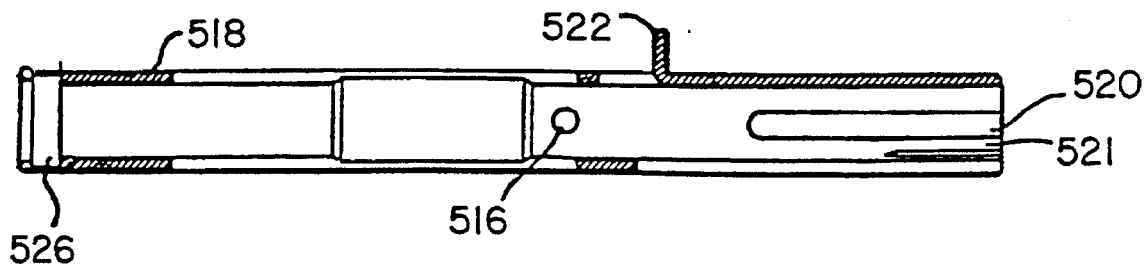

As shown in FIG. 27C, a side cross section view of the frame clamp tube, the distal end of frame clamp tube 518 includes a circumferential recess 526 configured and dimensioned to receive clamp tube snap 564. FIG. 27D is a partial rear side view of the clamp tube showing the proximal end of the clamp tube. As there shown, the rear side of clamp tube 518 includes a leaf spring slot 520 and a leaf spring cam 521. FIG. 27E is a partial rotated view of tube 518 showing cam 521. As shown, cam 521 is formed by bending a section of the tube wall to protrude outward from the circumference of the tube. Frame clamp tube 518 is longitudinally movable from the proximal position shown in FIG. 24 to a distal position to close the instrument jaws. The distal end of a clamp tube spring 519 engages spring retaining pin 522 and the proximal end of clamp tube spring 519 engages the screw mount 497. Thus, clamp tube spring 519 retains the frame clamp tube in the proximal position until force is exerted to move the tube to the distal position. As shown in FIG. 24, the distal end of frame clamp tube 518 is disposed within outer tube 494. In the proximal clamp tube position there illustrated, the distal end of the frame clamp tube is substantially aligned with the distal end of the cylindrical barrel of outer tube 494.

Figure 29:
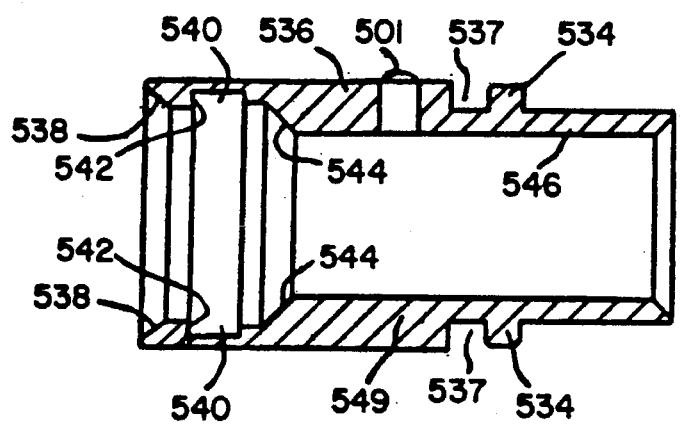
FIG. 29 illustrates a sectional side view of the outer tube of the first alternative embodiment.

Referring now to FIGS. 24 and 29, outer tube 494 is substantially cylindrical and engages the distal opening in frame 474. The proximal, frame engaging portion of outer tube 494 includes an annular flange 534 which, together a distal outer tube body section 536, define an annular groove 537 for receiving inward flange 500 at the distal end of frame 474. Longitudinal ribs 502 on the frame (shown in phantom) engage the exterior outer tube surface to stabilize outer tube 494 relative to frame 474. Outer tube 494 is fixed relative to frame 474, as by compression fit and/or locking engagement of one or more corresponding sets of pins and holes, etc. Thus, outer tube 494 projects from the distal end of frame 474 but is fixed relative to the frame. The projecting distal end of outer tube 494 is configured and dimensioned to engage collet 402 on the endoscopic portion of the instrument (see FIG. 17). The outer diameter of body section 536 is configured and dimensioned to be inserted into sleeve 422, with collet fingers 410 simultaneously urged within outer tube 494 by inwardly inclined rim 538. As shown in FIG. 29, body section 536 includes collet finger recesses 540 having slightly inclined distal walls 542. Body section 536 further includes transition walls 544 between the collet finger receiving portion and the cylindrical barrel section 546. Cylindrical barrel section 546 has a uniform diameter from the proximal termination point of inclined walls 544 to the proximal end of outer tube 494. As stated, cylindrical barrel section 546 receives frame clamp tube 518 in concentric longitudinal sliding relation (see FIG. 24). The protruding distal portion of outer tube 494 also includes a small bump, protrusion or detent pin 501 for engaging one of detent slots 503 on the inner surface of sleeve 522 (see FIG. 20), such that sleeve 522 may be rotated between distinct detent positions relative to outer tube 494.

Figure 30B:
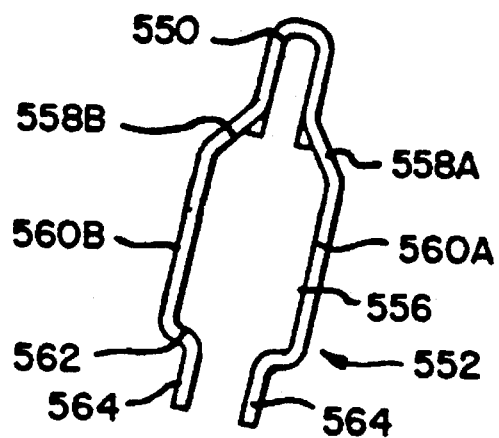
FIGS. 30A and 30B illustrate side and distal end views, respectively, of the outer handle of the first alternative embodiment.
Figure 30A:
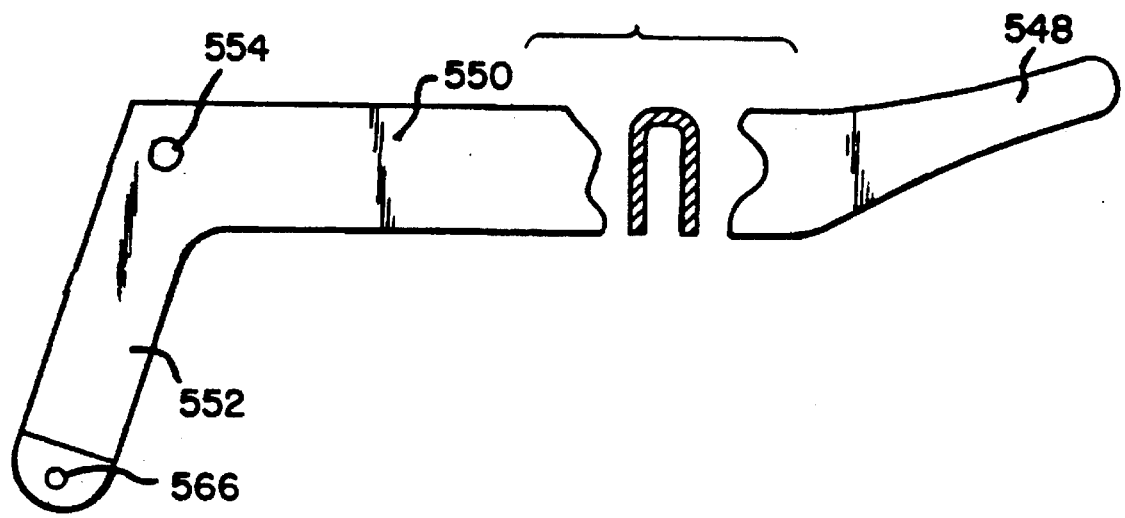

Outer handle 472 includes a proximal tab portion 548, a longitudinal arm portion 550, and a lever arm portion 552 (see FIGS. 24, 30A and 30B). The proximal end of longitudinal arm portion 552 terminates in tab 548, and the distal end of arm portion 550 includes a hinge pin aperture 554 for receiving hinge pin 486 (see FIG. 24).

As shown in FIGS. 30A and 30B, outer handle arm 518 is of substantially U-shaped configuration such that inner handle arm 508 may be received within the open interior of longitudinal arm section 550. Outer handle lever arm portion 552 is configured and dimensioned to have an open interior section 556 which surrounds the inner handle lever arm portion and clamp tube assembly. Open interior section 556 permits unrestricted longitudinal movement of the frame clamp tube in response to inner handle 470 independent from the action of the outer handle. To obtain open interior section 556, outer handle lever arm portion 552 includes outwardly flared regions 558A, 558B, substantially parallel body walls 560A, 560B and a neck region 562 terminating at distal end portions 564. Referring to FIG. 30A, each distal end portion 564 includes a sprocket wheel pin receiving aperture 566.

Referring again to FIG. 24, a sprocket wheel 568 is mounted on sprocket wheel pin 566 and engages a chain 570. One end of chain 570 is fixed to frame 474, as by being secured to a pin mount 572. The other end of chain 570 is fixed to a chain engaging tab 574. Chain engaging tab 574 is attached as a downwardly extending tab at the proximal end of a drive tube 576. Drive tube 576 is disposed within frame clamp tube 518 and slides freely relative thereto. As will be appreciated, when outer handle 472 is closed toward the upper frame surface 482 outer handle lever portion 552 is rotated in the distal direction. This motion causes sprocket wheel 568 to follow an arcuate path, within the open bottom region 592 of the frame, drawing chain 570 and, consequently, drive tube 576 in the distal direction. It will be noted that elongated opening 524 on the bottom of frame clamp tube 518 accommodates chain 570 to ensure free movement of the chain and frame clamp tube relative to each other. In addition, a drive tube spring 577 engages frame screw mount 499 and a pin (not shown) within drive tube 576 to retain the drive tube in the proximal position shown until the instrument is fired.

Figure 31:
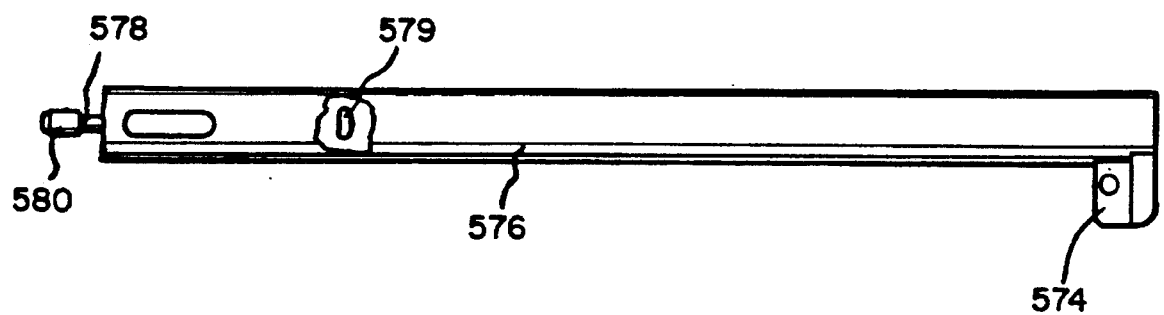
FIG. 31 illustrates a side view of a drive tube in accordance with the first alternative embodiment.

Briefly turning to FIG. 31, a side view of drive tube 576, the distal end of drive tube 576 is provided with an axially mounted protruding stem 578 bearing a push plug 580. Push plug 580 has a chamfered distal tip and is configured and dimensioned to be received between the proximal fingers 468 on channel adaptor 406 (see FIG. 17). As shown in the sectional portion of FIG. 31, the rear wall of drive tube 576 is provided with a safety locking slot 579.

Figure 32A:
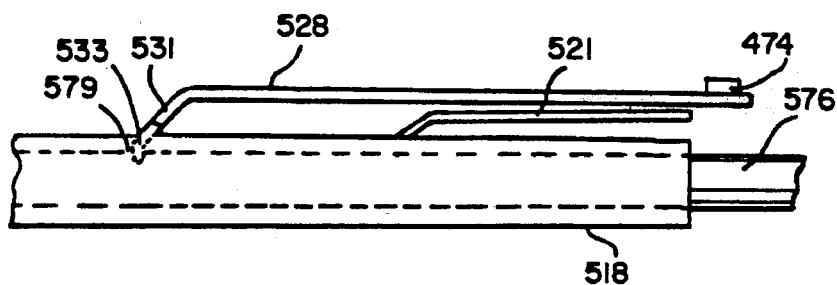
FIGS. 32A and 32B are top plan views of the frame clamp tube, drive tube and leaf spring illustrating proximal and distal frame clamp tube positions.
Figure 32B:
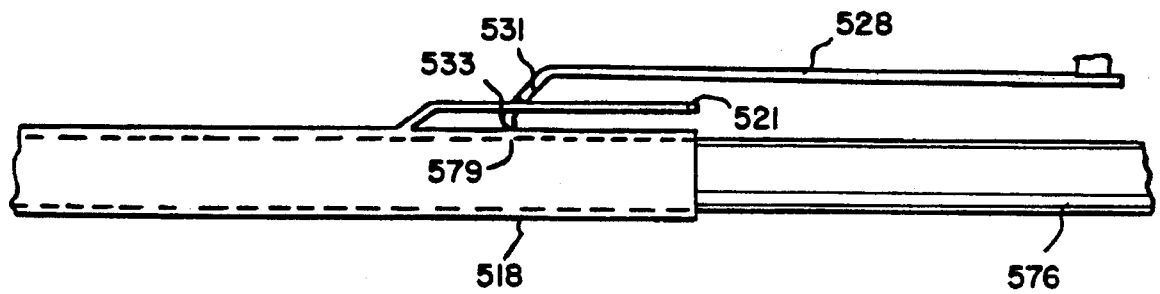

Advantageously, a safety locking mechanism is provided in this embodiment to prevent accidental firing of the instrument. Referring to FIGS. 28A and 28B, a leaf spring 528 is provided having a shank portion 529 and a curved tip 530. Curved tip 530 includes curved tip shoulders 531 of equal width to shank portion 529 extending approximately half the length of curved tip 530. Curved tip 530 further includes a central drive tube locking tip 533 protruding the full length of curved tip 530. Referring again to FIG. 24, the central region 532 outlined in phantom is a further partial sectional view looking beyond the far wall of drive tube 576. This relationship is better illustrated in FIGS. 32A and 32B, which are top plan views showing the frame clamp tube 518 in proximal and distal positions, respectively, relative to leaf spring 528. Leaf spring 528 is mounted to frame 474, as by screw mounting through screw hole 535 (see FIG. 28B), with curved tip 530 extending and biased toward frame clamp tube 518 and drive tube 576. In the proximal positions of tubes 518, 576, drive tube locking pin 533 extends through slot 520 on the far side of frame clamp tube 518 (see FIGS. 27D and 32A) and engages safety locking slot 579 on drive tube 576 (shown in phantom in FIG. 32A). Thus, in the proximal position, leaf spring 528 and locking pin 533 securely lock the drive tube in the proximal position and the instrument cannot be fired. However, leaf spring shoulder portions 531 do not extend into slot 520, but rather ride outside and to either side of slot 520. As frame clamp tube 518 moves from the proximal to the distal position, one of shoulder portions 531 rides onto leaf spring cam 521, thereby forcing leaf spring 528 away from tubes 518, 576 and disengaging locking pin 533 from safety locking slot 579 (see FIG. 32B). The leaf spring remains disengaged from the drive tube while the frame clamp tube is in the distal position, and returns to locking engagement with drive tube 576 whenever frame clamp tube 518 is returned to the proximal position. Advantageously, the force exerted by leaf spring 528 against cam 521 also tends to retain frame clamp tube 518 in the distal position, so that the instrument will remain in the clamping position in preparation for firing. In the position shown in FIG. 32B, frame clamping tube 518 is in the distal position to clamp the instrument jaws closed, but drive tube 576 remains in the proximal position. However, because safety locking pin 533 is disengaged from slot 579 (shown in phantom), the outer handle may now be closed to move drive tube 576 distally to fire the instrument.

In order to assemble the frame and endoscopic portions of the instrument constructed in accordance with this embodiment, outer tube 494 is axially aligned with and inserted into sleeve 522 until collet fingers 510, and more specifically annular flanges 416 on the collet fingers, engage collet finger recesses 540. In addition, as outer tube 494 is inserted into sleeve 522, (i) clamp tube snap 564 is inserted into frame clamp tube 518 and mates with corresponding recesses 526 of the frame clamp tube; and (ii) channel adaptor 406 is axially inserted through the frame clamp tube until push plug 580 is seated between channel adaptor fingers 468.

It will be noted that, in this embodiment, endoscopic portion 300 can be rotated relative to frame 301 by exerting rotational force on sleeve 422. As stated, detent pin 501 and detent slots 503 on the outer tube and sleeve, respectively, define distinct rotational positions of the endoscope portion relative to the frame. As the endoscopic portion rotates, collet 402 rotates relative to outer tube 494, clamp tube snap 564 rotates within frame clamp tube 518, and push plug 580 rotates within channel adaptor fingers 468. It will further be noted that in the starting position of the handles illustrated in FIG. 24, springs 519, 577 bias the frame clamp tube and drive tube into their proximal positions. The related mechanical linkages also urge handles 470, 472 into the open positions illustrated. Drive tube locking pin 533 engages drive tube safety locking slot 579 to lock the drive tube in the proximal position and, hence, handle 572 in the open position, until the instrument jaws are clamped closed.

Tissue clamping is effected by closing inner handle 470 against upper frame surface 482. As inner handle 470 pivots about hinge pin 486, pins 516 travel in slots 514 to draw frame clamp tube 518 in the distal direction, overcoming the force of the frame clamp tube spring 519 to advance frame clamp tube 518 to its distal position. Because frame clamp tube 518 engages clamp tube snap 564, movement of frame clamp tube 518 imparts longitudinal motion to clamp tube 327, thereby closing anvil 336 against the tissue engaging surface of cartridge 337. Moving the frame clamp tube to the distal position also causes leaf spring cam 521 on frame clamp tube 518 to engage and urge leaf spring 528 away from drive tube 576, thereby disengaging drive tube locking pin 533 from safety locking slot 579.

Thereafter, the instrument may be fired by closing outer handle 472 against the inner handle and frame. During this motion, sprocket wheel 568, via chain 570, overcomes the force of drive tube spring 577 and imparts distal longitudinal motion to drive tube 576 and, hence, to channel adaptor 406. Of course, distal longitudinal motion of channel adaptor 406 drives channel 329, cams 331 and knife 332 to eject staples from the cartridge and form an incision between the rows of staples placed.

In this embodiment, endoscopic portion 300 may be detached from frame and handle portion 301 by exerting distal force on sleeve 422. As previously stated, during such motion inclined surfaces 414, 436 cooperate to flex the collet fingers inward, thereby releasing the collet from outer tube 494. Collet fingers 410 in turn flex clamp tube snap 464 to disengage the clamp tube snap from the frame clamp tube. Finally, as sufficient withdrawing force is developed, the distally inclined surfaces of channel adaptor fingers 468 cause the channel adaptor fingers 468 to release push plug 580, thereby permitting full disengagement of the endoscopic portion from the frame. Of course, the withdrawing force required to release channel adaptor fingers 468 should be sufficiently great that opening outer handle 472 after firing the instrument does not result in disengagement of the push plug from the channel adaptor.

Advantageously, the double-handle and safety locking pin arrangement of this embodiment prevents accidental firing of the instrument with the jaws in the open position. That is, because the outer firing handle is mounted over the clamping handle and cannot be closed without previously and independently closing the inner clamping handle, it is impossible to fire the instrument until the jaws are fully closed to clamp tissue.

Further alternative embodiments are contemplated in which all or part of the instrument would be disposable. Where the entire instrument constitutes a single use, disposable instrument, the endoscopic portion preferably would be integral with the frame and as much of the instrument as possible would be constructed of plastic. In other contemplated embodiments the cartridge, knife and possibly the anvil might be disposable, alone or as a unit. It is also contemplated, for example, that a replaceable cartridge assembly could be provided which includes the knife and possibly the cam bars.

It is also preferred in all embodiments to include a sealing member within the housing in order to effect an internal seal within the housing. Of course, such a sealing member, not here illustrated, must permit longitudinal movement of the clamping and firing elements.

Suitable materials for use in constructing the instrument in accordance with the invention include stainless steel, titanium, aluminum and plastic. Where disposability of all or part of the instrument is desired, plastic is the material of choice for economic reasons. Plastic is also preferred, where possible, in order to minimize the overall weight of the instrument. Of course, certain parts, such as the anvil, have performance requirements which dictate the material used. In the case of the anvil, the need for high strength and accurately shaped depressions to deform the staples typically requires use of a metal, such as stainless steel. Similarly, the knife requires a fine cutting edge and typically is also made from stainless steel. The staples used with the present invention may be non-absorbable plastic or metal or an absorbable synthetic material, such as a copolymer of polyglycolic acid. Of course, the foregoing identification of materials is exemplary only, and numerous variations, substitutions and changes in material will occur to those of ordinary skill in the art.

OPERATION OF THE INSTRUMENT

In use, the endoscopic portion of the instrument is inserted into the body, preferably through an endoscopic tube. It is further preferred that the endoscopic tube apparatus be capable of maintaining a sealed pneumoperitoneum, with the internal sealing member of the housing further maintaining this seal despite introduction of the instrument in accordance with the invention into the endoscopic tube. As a practical matter, the jaws of the instrument are closed for insertion into the endoscopic tube, either by pinching the anvil and cartridge prior to insertion or by closing the clamping mechanism prior to insertion.

After insertion into the endoscopic tube, the endoscopic portion may be rotated in order to appropriately orient the instrument at the stapling site. Rotation of the endoscopic portion relative to the body may be attained by rotating the instrument, as a whole, by rotating the endoscopic portion relative to the frame using finger wheel 123 (see FIG. 1) or sleeve 522 (see FIG. 17), or any combination thereof.

Referring additionally now to FIGS. 15A and 15B, with the instruments properly oriented so that the tissue to be fastened 201, 202 is disposed between the open jaws of the instrument, i.e., between the tissue contacting surfaces of anvil member 136, 336 and cartridge 137, 337, the jaws are closed to clamp the tissue. In the first embodiment, the surgeon presses down on toggle lever 104, thereby sliding collar 127 distally, via collar shaft 125, collar pivot wheel 115, collar pivot holder 112, and collar moving pivot 111. As collar 127 moves distally in the direction of arrow A from a first position where the camming edge 127B at the distal end of collar 127 is proximal to hinge 136C (FIG. 15A), to a second position where the camming surface 127B is distal to the hinge 136C (FIG. 15B), the camming edge 127B contacts the upper surface of the anvil arms 136B, thereby forcing anvil member 136 to rotate in the direction of arrow B until the fastener forming surface 136E is brought into close cooperative alignment with the cartridge assembly, i.e., the slots 137A are aligned with staple forming depressions 136D. FIG. 15B illustrates the instrument with the jaws in a closed position. In the second embodiment described above, the same result is obtained by closing inner handle 470 to impart longitudinal motion to frame clamping tube 518 and clamping tube 337, thereby close anvil 336 against cartridge 337. It is contemplated that achieving proper instrument placement may require multiple attempts to clamp the tissue prior to firing the instrument.

After closing the instrument jaws, the instrument is ready to be fired. To fire the instrument in the first embodiment, the surgeon presses push button 117, whereby the knife 132 and cam bars 131 are driven longitudinally through the cartridge via cam bar channel 129, channel pivot 122, channel pin holder 121, and firing support shaft 117. As explained above, as the cam bars 131 are driven longitudinally through the cartridge, the staple drive members 139 push staples 138 through the body tissue against anvil 136, where the staples 138 are crimped. In the second described embodiment, outer handle 472 is closed to impart longitudinal motion to drive tube 576, channel 329, cams 331 and knife 332 to fire the staples and make an incision.

It will be understood that various modifications can be made to the various embodiments of the present invention herein disclosed without departing from the spirit and scope thereof. For example, various sizes of the instrument are contemplated, as well as various types of construction materials. Also, various modifications may be made in the configuration of the parts. For example, in the first embodiment the elongated slot for allowing access to the thumbwheel may be placed alternatively in the left body portion or right body portion. Therefore the above description should not be construed as limiting the invention but merely as

What is claimed is:

1. A method of endoscopically driving fasteners into body tissue comprising the steps of:

provioding an endoscopic opening into a body for accessing tissue to be fastened;

providing a surgical apparatus for driving surgical fasteners into body tissue including:

a frame which includes first and second actuating handles, each actuating handle pivotally mounted with respect to a pivot pin and movable between a first and second position;

an endoscopic portion defining a longitudinal axis and extending distally from said frame, said endoscopic portion including:

i) an elongated support for receiving a cartridge assembly, the cartridge assembly having a distal end and a proximal end and including a plurality of surgical fasteners slidably mounted therein, and having a tissue engaging surface;

ii) a jaw member having a distal end and a proximal end, said proximal end of said jaw member being pivotally retained in said elongated support such that the jaw member is movable between an open position and a closed position in close cooperative alignment with the tissue engaging surface of the cartridge assembly and said distal end of said jaw member is in juxtaposed alignment with said distal end of said cartridge assembly;

iii) a closure member for moving the jaw member between the open position and the closed position comprising a collar operatively associated with at least a portion of said support and said jaw member, said collar having a camming edge and being movable between a first position in which said camming edge is located proximally to the proximal end of said jaw member, and a second position in which said camming edge is located distally to the proximal end of said jaw member, said collar cooperating with said jaw member such that when said collar is moved from said first position to said second position, said jaw member is urged to said closed position;

iv) pusher elements for ejecting the surgical fasteners from the cartridge assembly through tissue; and v) an elongated member operatively associated with said second actuating member which translates with respect to said endoscopic portion independent of said closure member for actuating said pusher elements; and vi) linkage operatively associated with said first actuating handle for moving said collar between said first position and said second position;

pivoting said first actuating handle from said first to said second position, thereby translating the closure member to the second position to approximate said jaw member towards said cartridge assembly prior to inserting said jaw member and cartridge assembly into said endoscopic opening;

inserting said approximated jaw member and cartridge assembly of said surgical apparatus into said endoscopic opening;

pivoting said first actuating handle from said second position to said first position, thereby translating the closure member from the second position to the first position to open said approximated jaw member and said cartridge assembly to define a tissue receiving space therebetween;

positioning body tissue into which said fasteners are to be driven such that said body tissue enters said tissue receiving space between said jaw member and said cartridge assembly in a direction extending from a distal to a proximal end of said jaw member and said cartridge assembly;

pivoting said first actuating handle from said first position to said second position, thereby translating the closure member back to the second position to cause said jaw member to move said jaw member from said open position to said closed position; and pivoting said second actuating handle from said first position to said second position, thereby translating said elongated member independent of the closure member and actuating said pusher elements for ejecting said surgical fasteners from said cartridge assembly to drive said surgical fasteners into said body tissue.

2. The method of endoscopically driving fasteners into body tissue of claim 1, wherein the step of providing an endoscopic opening further comprises:

providing an endoscopic tube for insertion into a body to access body tissue to be fastened and inserting said endoscopic tube into said body to access tissue to be fastened.

* * * * *